United States Patent
Nedergaard et al.

(10) Patent No.: US 12,311,035 B2
(45) Date of Patent: May 27, 2025

(54) GLYMPHATIC DELIVERY BY MANIPULATING PLASMA OSMOLARITY

(71) Applicant: University of Rochester, Rochester, NY (US)

(72) Inventors: Maiken Nedergaard, Rochester, NY (US); Benjamin Plog, Rochester, NY (US); Humberto Mestre Payne, Rochester, NY (US)

(73) Assignee: University of Rochester, Rochester, NY (US)

( * ) Notice: Subject to any disclaimer, the term of this patent is extended or adjusted under 35 U.S.C. 154(b) by 537 days.

(21) Appl. No.: 17/280,606

(22) PCT Filed: Sep. 30, 2019

(86) PCT No.: PCT/US2019/053808
§ 371 (c)(1),
(2) Date: Mar. 26, 2021

(87) PCT Pub. No.: WO2020/072357
PCT Pub. Date: Apr. 9, 2020

(65) Prior Publication Data
US 2022/0031867 A1     Feb. 3, 2022

Related U.S. Application Data

(60) Provisional application No. 62/741,295, filed on Oct. 4, 2018.

(51) Int. Cl.
    *A61K 49/00*       (2006.01)
    *A61K 9/00*       (2006.01)
    *A61K 45/06*       (2006.01)

(52) U.S. Cl.
CPC ........ *A61K 49/0058* (2013.01); *A61K 9/0085* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,901,650 B2 | 2/2018 | Nedergaard et al. | |
| 2017/0105927 A1* | 4/2017 | Thorne | C07K 16/00 |
| 2017/0145076 A1 | 5/2017 | Curran et al. | |
| 2017/0202931 A1* | 7/2017 | DeKelver | C12N 15/102 |
| 2018/0002722 A1 | 1/2018 | Asokan et al. | |
| 2018/0134797 A1 | 5/2018 | Zhang et al. | |
| 2018/0237496 A1 | 8/2018 | Chen et al. | |
| 2018/0271796 A1 | 9/2018 | Zhang et al. | |

FOREIGN PATENT DOCUMENTS

| | | | | |
|---|---|---|---|---|
| CN | 105228652 A | 1/2016 | | |
| WO | WO-2014130777 A1 | * | 8/2014 | ............. A61B 5/055 |
| WO | WO-2017210343 A1 | * | 12/2017 | ......... A61K 38/1709 |
| WO | 2018015467 A1 | 1/2018 | | |

OTHER PUBLICATIONS

Robert G. L. Pullen, Michael Depasquale, and Helen F. Cserr; Bulk flow of cerebrospinal fluid into brain in response to acute hyperosmolality; Am. J. Physiol. 253 (Renal Fluid Electrolyte Physiol. 22): F538-F545, 1987 (Year: 1987).*
Michelle E. Pizzo; Intrathecal antibody distribution in the rat brain: surface diffusion, perivascular transport and osmotic enhancement of delivery; (J Physiol 596.3 (2018) pp. 445-475;first published online Oct. 12, 2017) (Year: 2017).*
Bulk Flow of Cerebrospinal Fluid into Brain in Response to Acute Hyperosmolality (hereinafter the article is referred as Pullen), Intrathecal Antibody Distribution in the Rat Brain: Surface diffusion, perivascular transport and osmotic enhancement of delivery; Robert G. L. Pullen, Am. J. Physiol. 253 (Year: 1987).*
Fowler, M. J. et al., "Intrathecal drug delivery in the era of nanomedicine"; Advanced Drug Delivery Reviews (2020); vol. 165-166; pp. 77-95.
Koffie, R. M. et al., "Nanoparticles enhance brain delivery of blood-brain barrier-impermeable probes for in vivo optical and magnetic resonance imaging"; PNAS (2011); vol. 108, No. 46; pp. 18837-18842.
Vulchanova, L. et al., "Differential adeno-associated virus mediated gene transfer to sensory neurons following intrathecal delivery by direct lumbar puncture"; Molecular Pain (2010); vol. 6; 9 pages.
Pullen, R. L. et al., "Bulk flow of cerebrospinal fluid into brain in response to acute hyperosmolality"; American Journal of Physiology (1987); vol. 253; pp. F538-F545.
Plog, B. A. et al., "The Glymphatic System in Central Nervous System Health and Disease: Past, Present and Future"; Annual Review of Pathology: Mechanisms of Disease (2018); vol. 13:1; pp. 379-394.
Russak, A. J et al., "Angiotensin II Increase Glymphatic Flow Through a Norepinephrine-Dependent Mechanisim"; Neurology Annual Meeting, AAN (2016); vol. 86:16, Suppl 1; p. P5.214.
Iliff, J. J., et al., "Cerebral Arterial Pulsation Drives Paravascular CFS-Interstitial Fluid Exchange in the Murine Brian"; The Journal of Neuroscience (2013); vol. 33:46, pp. 18190-18199.
Lundgaard, I. et al., "Beneficial Effects of Low Alcohol Exposure, but Adverse Effects of High Alcohol Intake on Glymphatic Function"; Scientific Reports (2018); vol. 8:1; 16 pgs.
Benveniste, H. et al., "Anesthesia with Dexmedetomidine and Low-Dose Isoflurane Increases Solute Transport via the Glymphatic Pathway in Rat Brain when Compared with High-Does Isoflurance"; Anesthesiology (2017); vol. 126:6; pp. 976-988.
Horiguchi, N. et al., "Liver Regeneration is Suppressed in Alcoholic Cirrhosis Correlation with Decreased STAT3 Activation"; Alcohol (2007); vol. 41; pp. 271-280.

(Continued)

*Primary Examiner* — Robert A Wax
*Assistant Examiner* — Andre Mach
(74) *Attorney, Agent, or Firm* — Fox Rothschild LLP

(57) ABSTRACT

This invention relates to improving delivery of agents to the central nervous system.

22 Claims, 21 Drawing Sheets

(56) References Cited

OTHER PUBLICATIONS

Starkel, P. et al., "Deficient Stat3 DNA-Binding is Associated with high Pias3 Expression and a Positive Anti-Apoptotic Balance in Human End-Stage Alcoholic and Hepatits C Cirrhosis"; Journal of Hepatology (2005); vol. 43:4; pp. 687-695.
Koffie, R. M. et al., "Nanoparticles Enhance Brain Delivery of Blood-Brain Barrier-Impermeable Probes for in vivo Optical and Magnetic Resonace Imaging"; PNAS (2011); vol. 108:46; pp. 18837-18842.
Thakker, D. R. et al., "Intracerebroventricular Amyloid-Beta Antibodies Reduce Cerebral Amyloid Angiopathy and Associates Micro-Hemorrhages in aged Tg2576 Mice"; PNAS (2009); vol. 106:11; pp. 4501-4506.
Sun, B. et al., "Lymphatic Drainage System of the Brain: A Novel Targe for Intervention of Neurological Diseases"; Progress in Neurobiology (2018); vol. 163: Sp., pp. 118-143.
Vulchanova, L. et al., "Differential Adeno-Associated Virus Mediated Gene Transfer to Sensory Neurons Following Intrathecal Delivery by Direct Lumbar Puncture"; Molecular Pain (2010); vol. 6:31, 9 pgs.
Sonoda, "BBB-penetrating technology" Farumashia, vol. 52, No. 11, 2016, pp. 1051-1053.
Wadghiri et al., "Detection of Alzheimer's Amyloid in Transgenic Mice Using Magnetic Resonance Microimaging", Magnetic Resonance in Medicine, vol. 50, pp. 293-302.

* cited by examiner

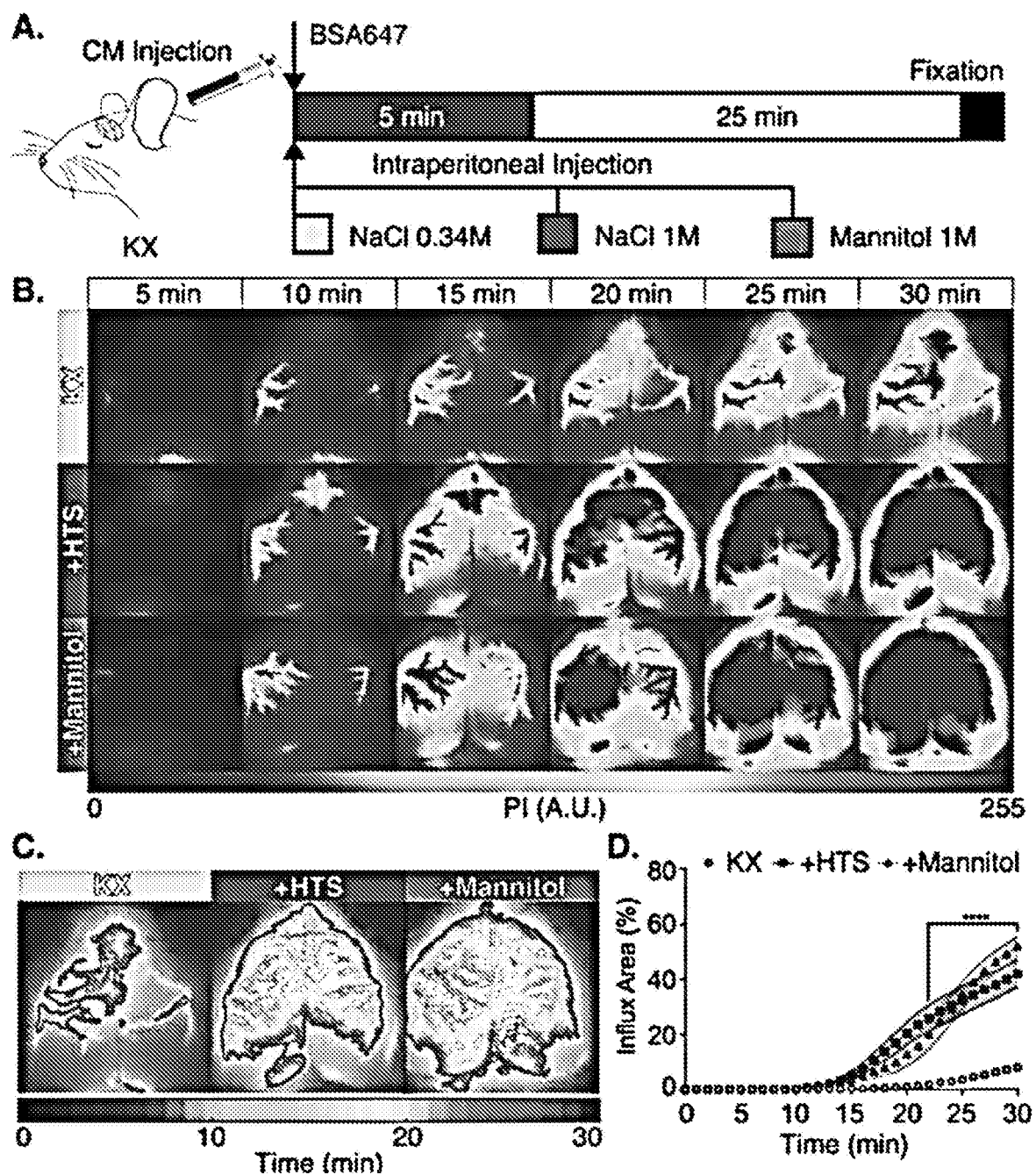
FIGS. 2A, 2B, 2C, and 2D

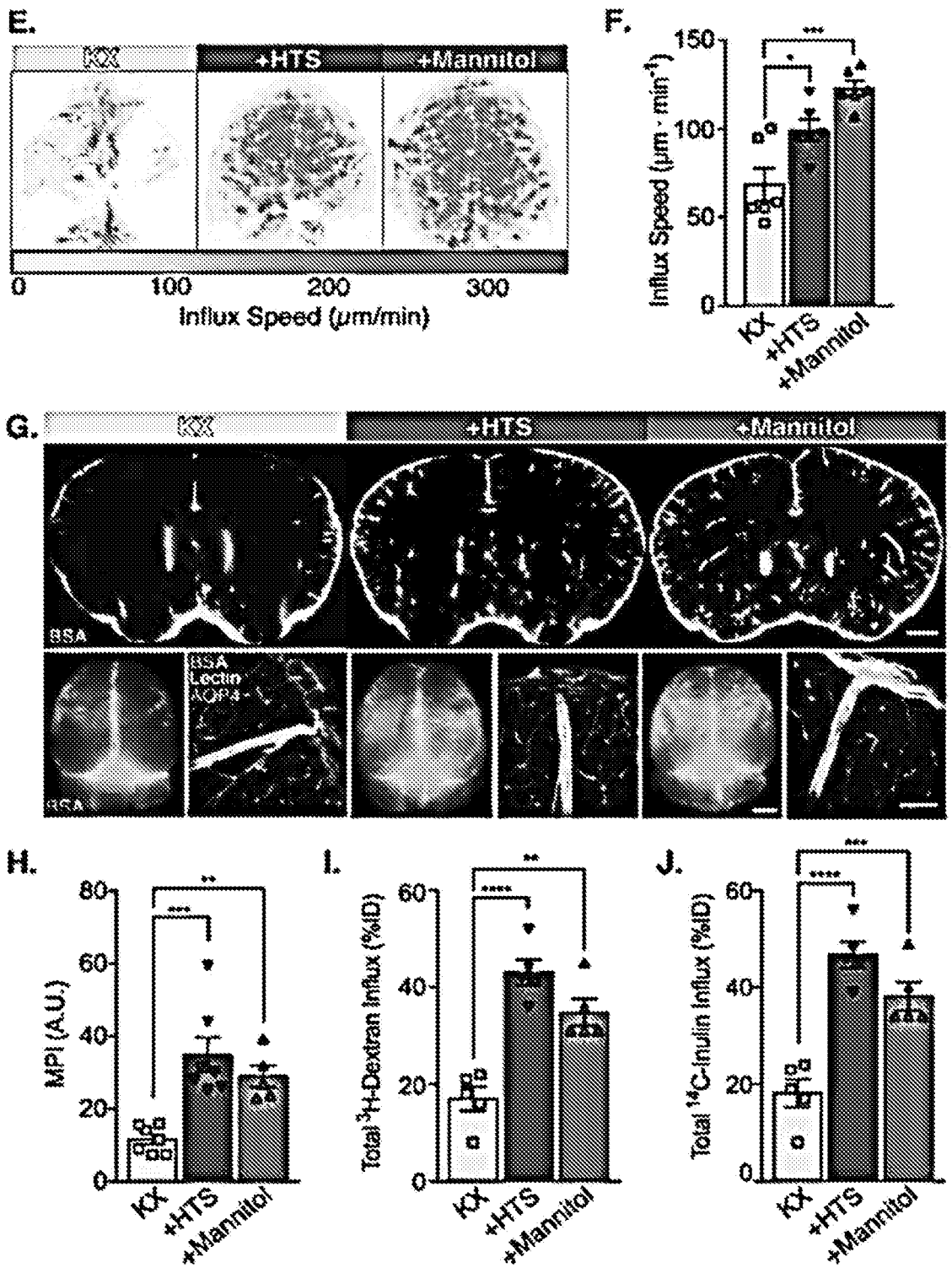
FIGS 2E, 2F, 2G. 2H, 2I, and 2J

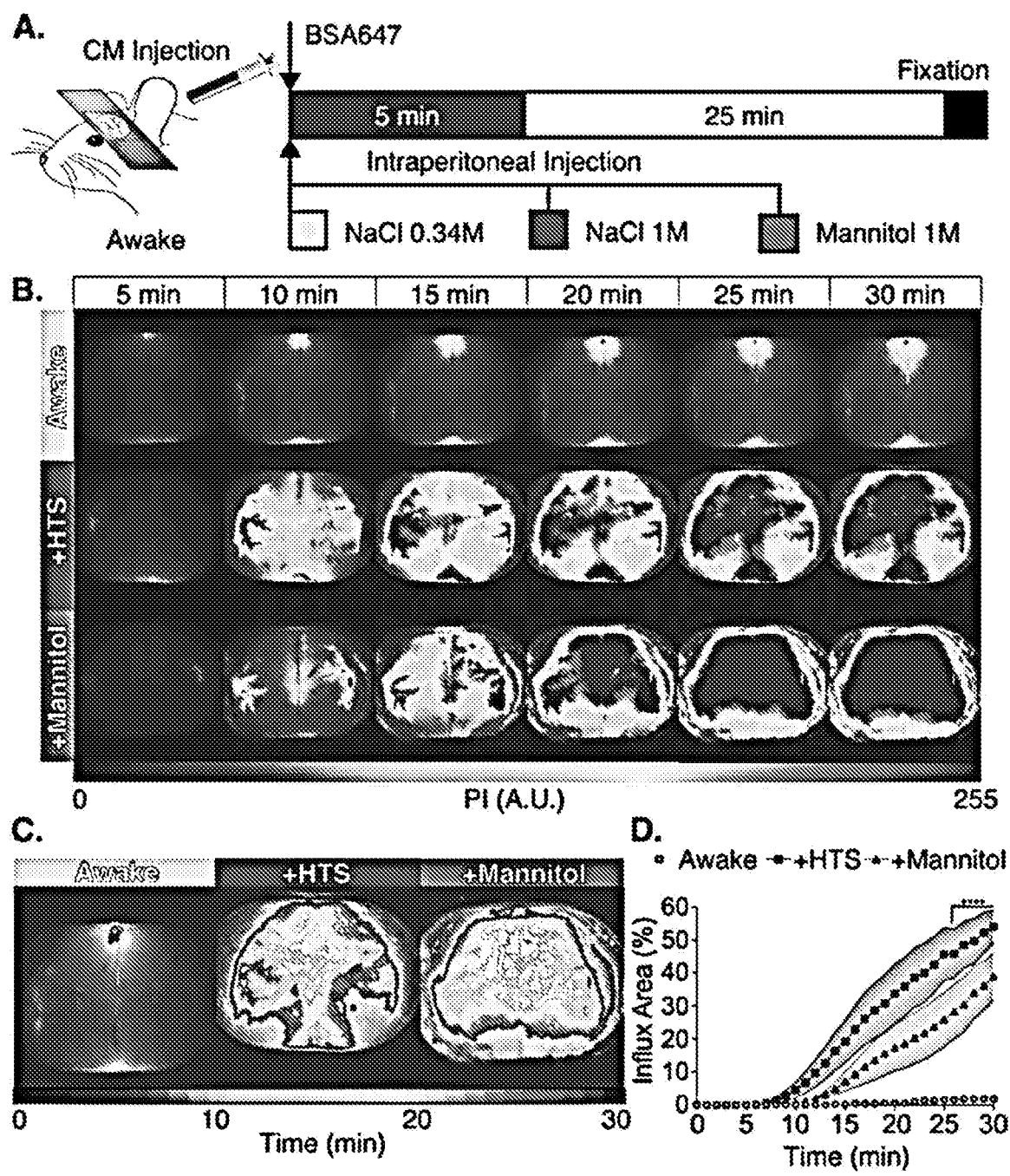
FIGS. 3A, 3B, 3C, and 3D

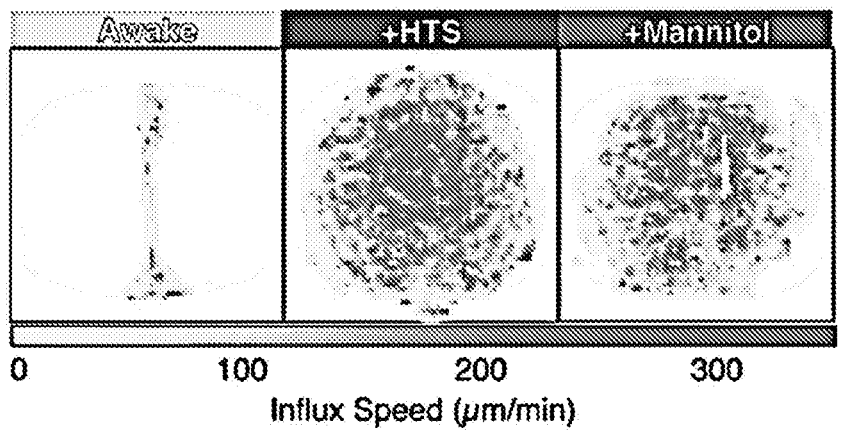
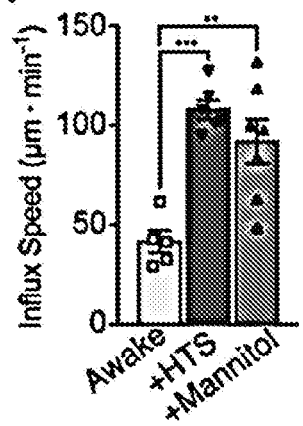
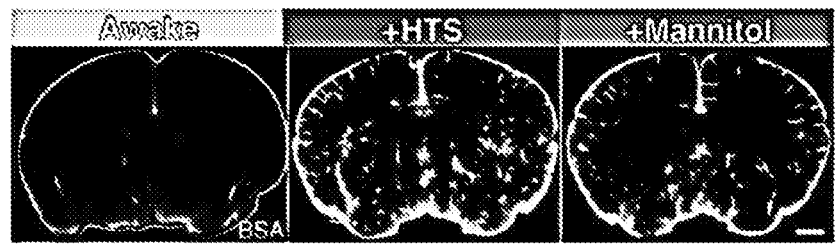
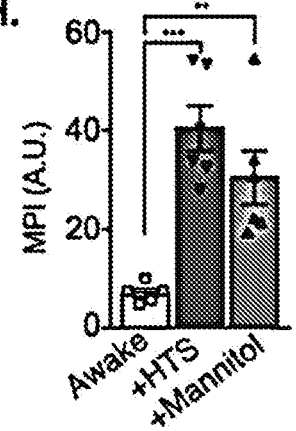
FIGS. 3E, 3F, 3G, and 3H

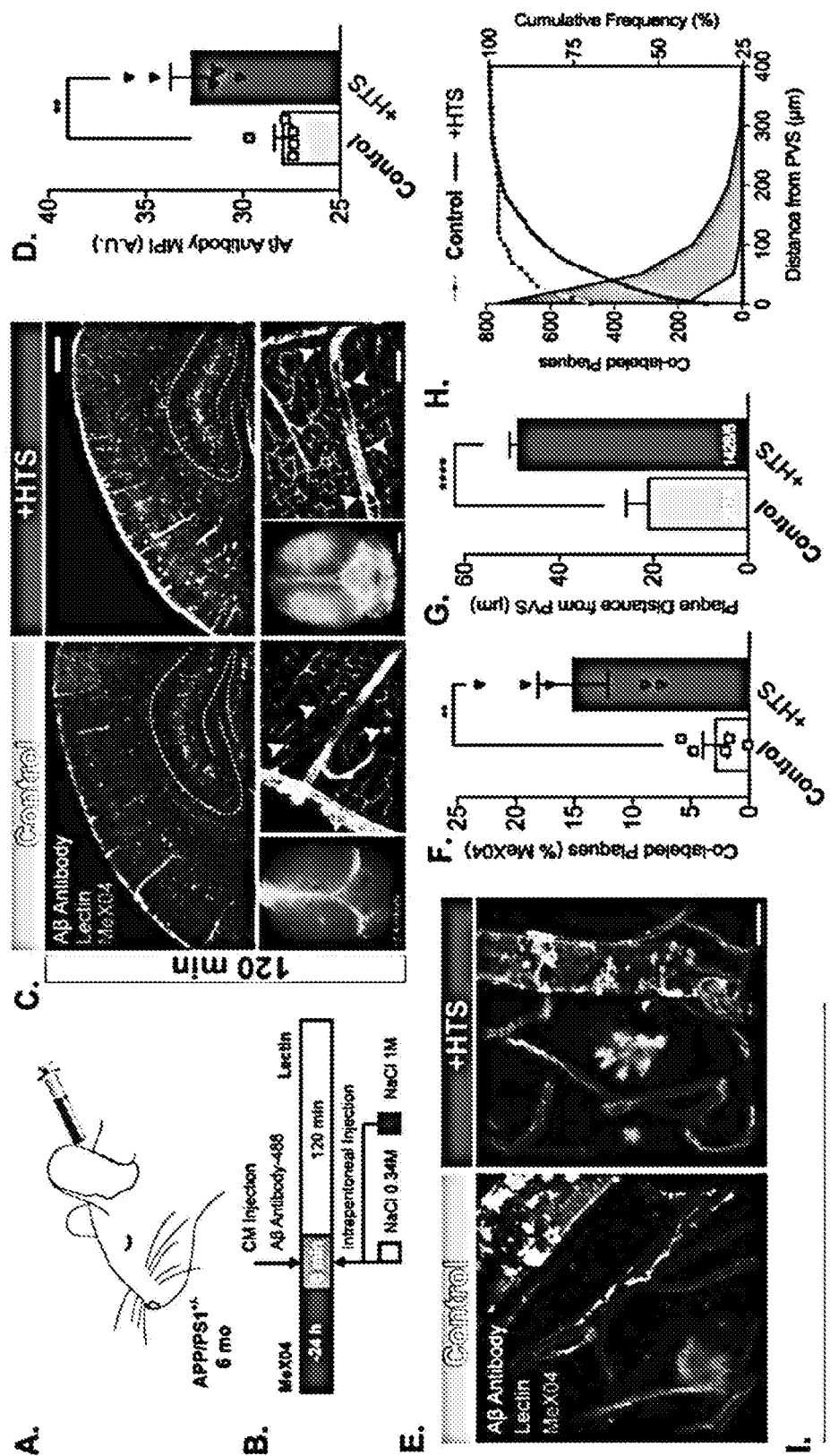
FIGs. 4A, 4B, 4C, 4D, 4E, 4F, 4G, and 4H

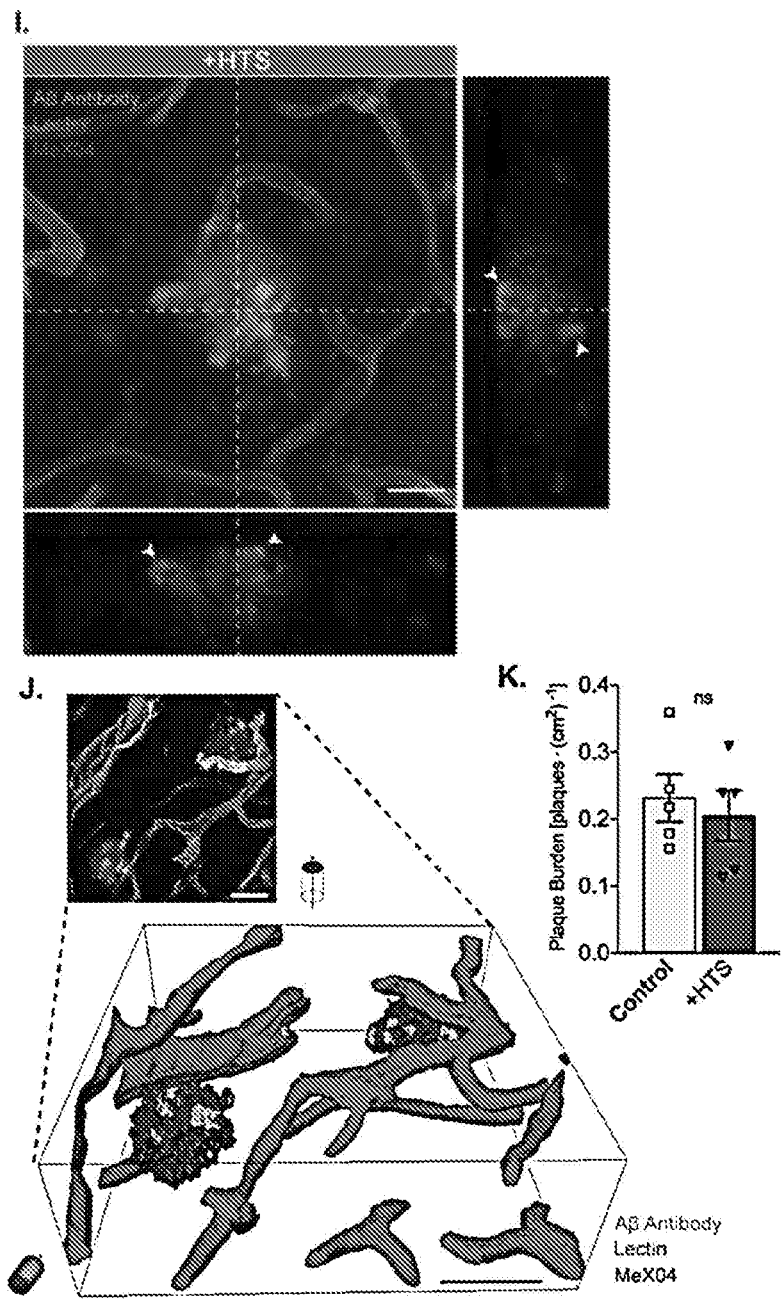
FIGS. 4I, 4J, and 4K

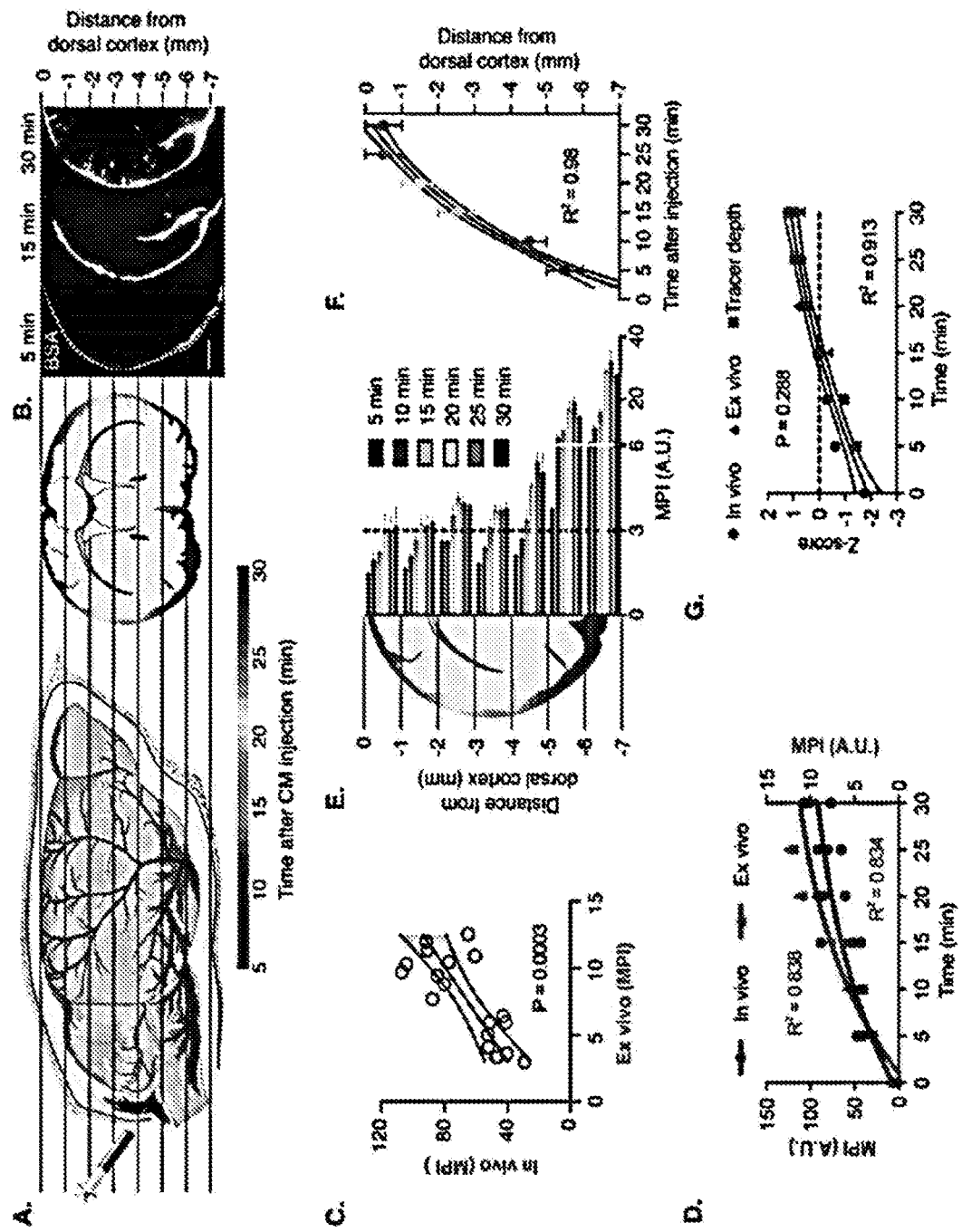
FIGS. 7A, 7B, 7C, 7D, 7E, 7F, and 7G

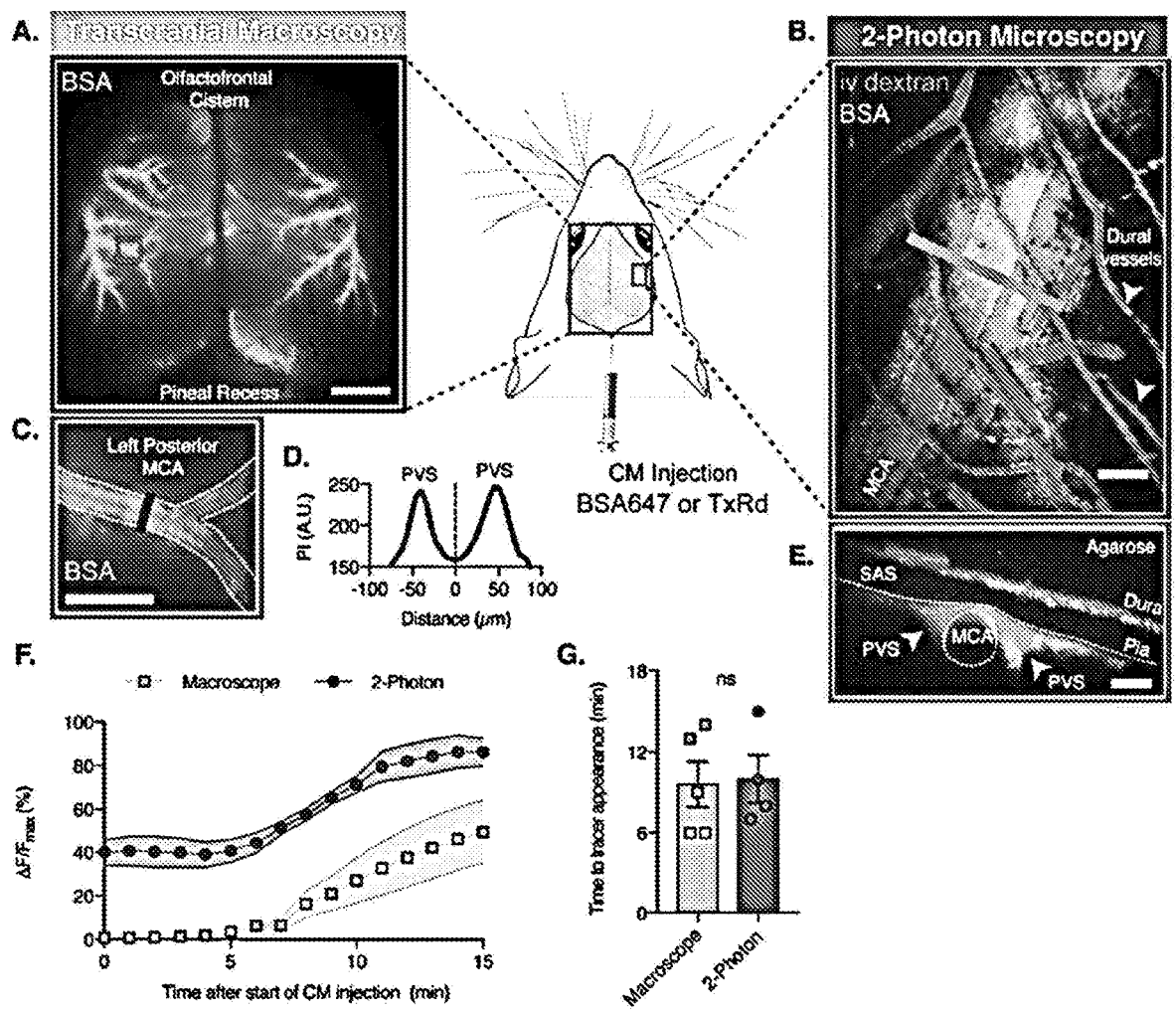
FIGS. 8A, 8B. 8C, 8D, 8E, 8F, and 8G

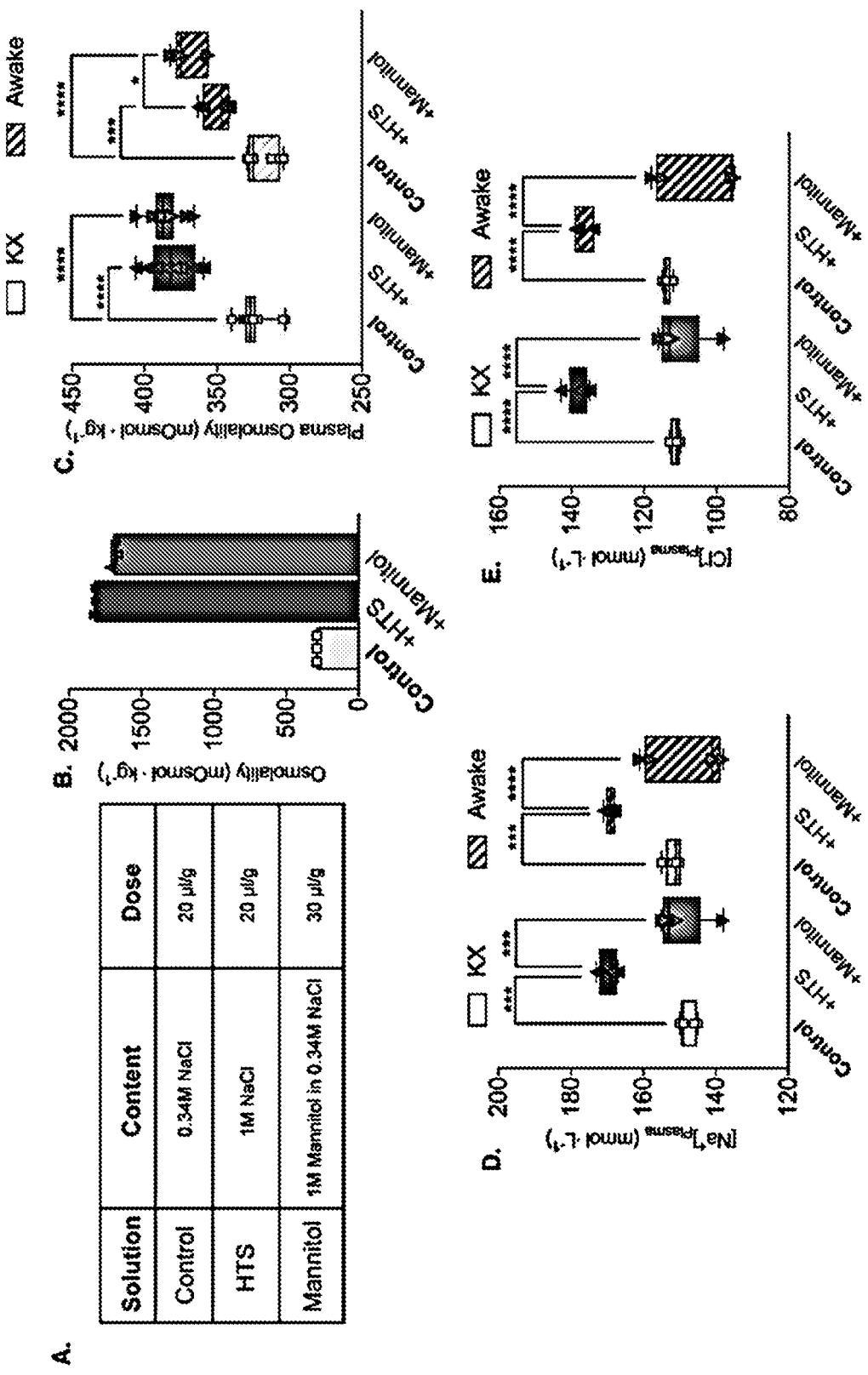
FIGS. 11A, 11B, 11C, 11D, and 11E

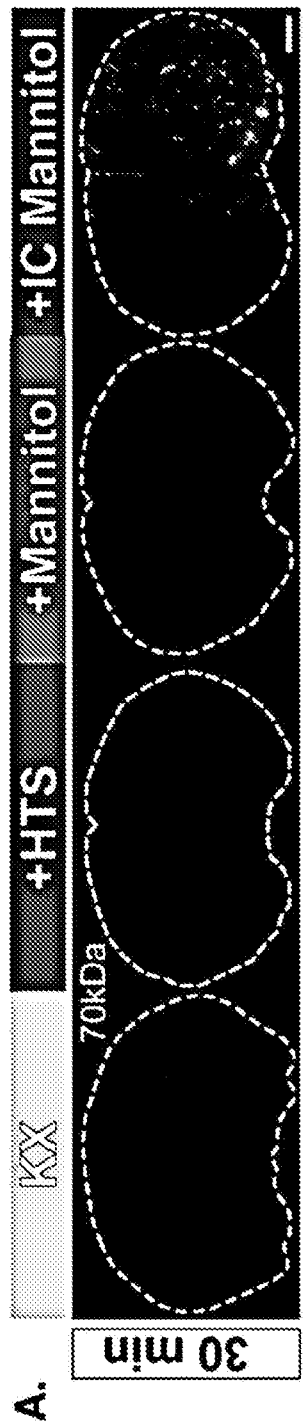
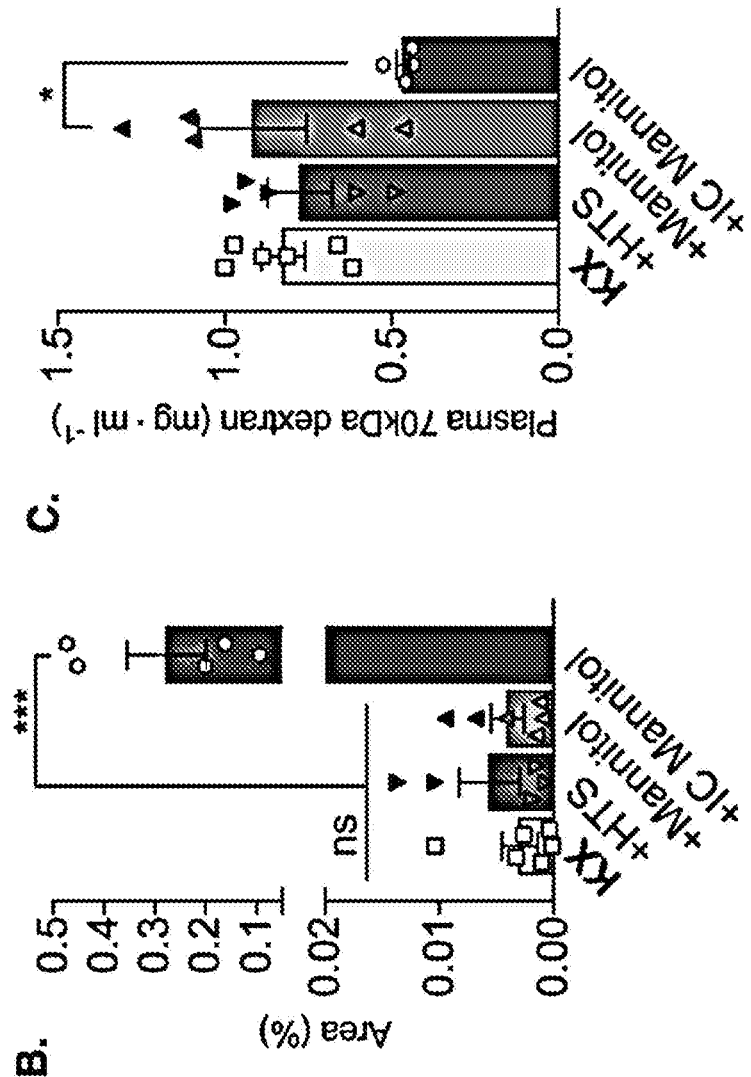
FIGs. 12A, 12B, and 12C

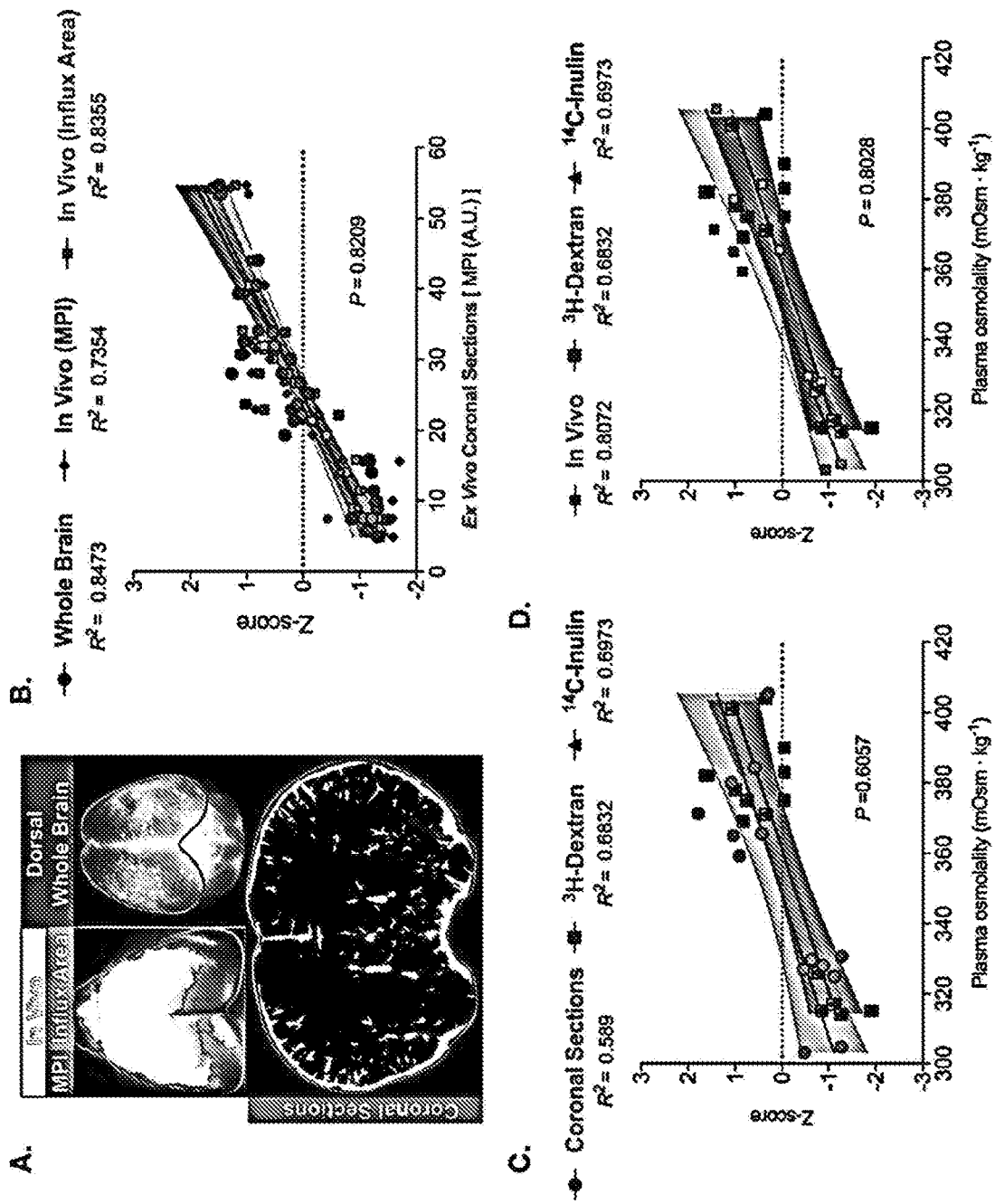
FIGS. 14A, 14B, 14C, and 14D

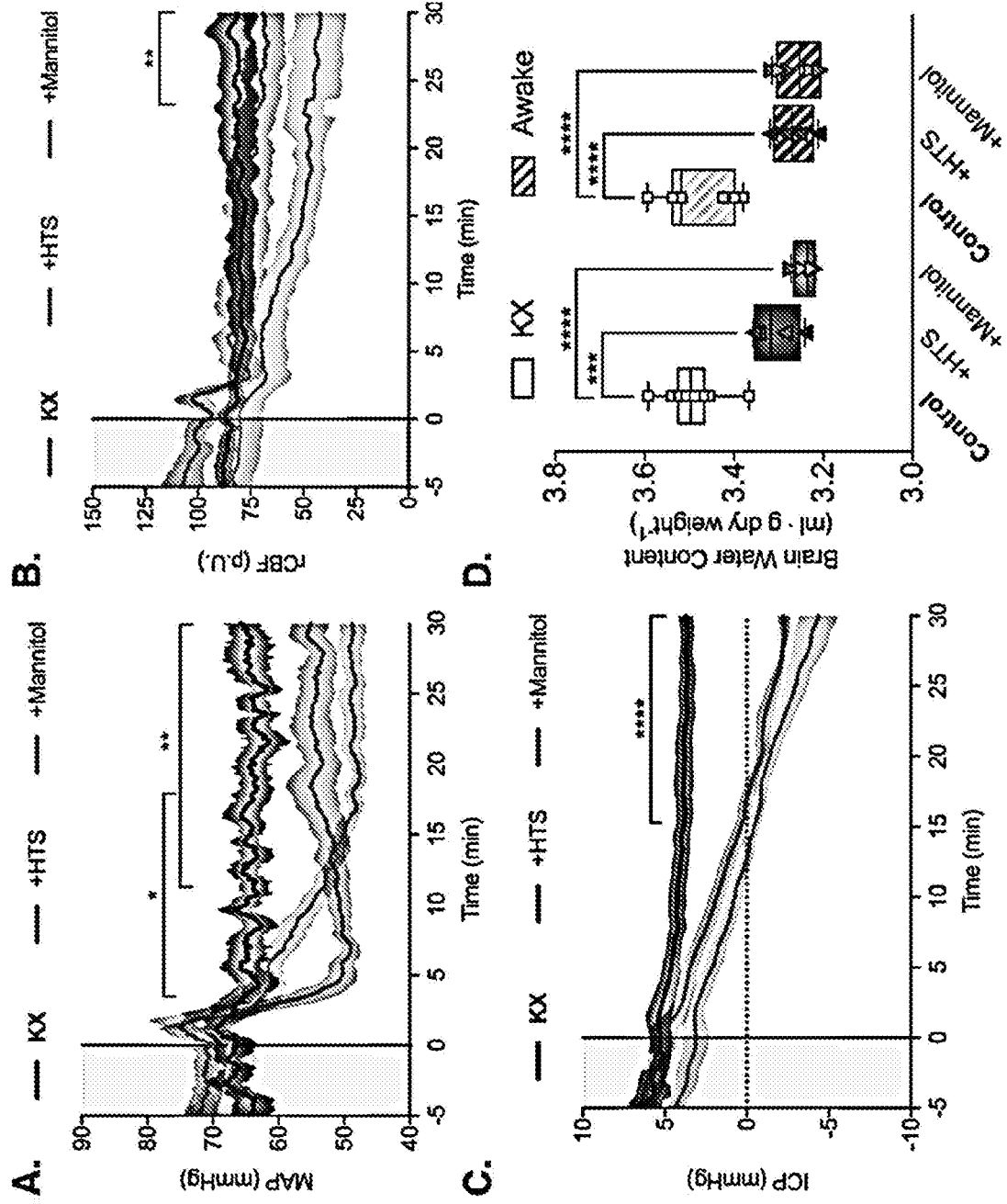
FIGS. 15A, 15B, 15C, and 15D

GLYMPHATIC DELIVERY BY MANIPULATING PLASMA OSMOLARITY

CROSS REFERENCE TO RELATED APPLICATION

This application is a U.S. National Phase of International Application No.: PCT/US2019/053808, filed Sep. 30, 2019, which claims priority to U.S. Provisional Application No. 62/741,295 filed on Oct. 4, 2018. The content of the application is incorporated herein by reference in its entirety.

GOVERNMENT INTERESTS

This invention was made with government support under R01NS100366 and RF1AG057575 awarded by National Institutes of Health and under W81XWH-16-1-0555 awarded by the Office of the Assistant Secretary of Defense for Health Affairs. The government has certain rights in the invention.

FIELD OF THE INVENTION

This invention relates to improving delivery of agents to the central nervous system.

BACKGROUND OF THE INVENTION

Various therapeutic agents have been developed for treating central nervous system (CNS) diseases. However, delivery therapeutic agents to the brain is severely limited by the largely impermeable blood-brain barrier (BBB) and poor penetration of the therapeutic agents to the brain. Improving the delivery of drugs to the CNS is a considerable clinical challenge (4, 19, 55), especially in the settings of immunotherapy. For example, therapies based on monoclonal antibodies (mAb) are currently being developed for CNS diseases such as Alzheimer's disease (AD) (1), Parkinson's disease (2), amyotrophic lateral sclerosis (ALS) (3), frontotemporal lobar dementia (FTLD)(4), and CNS tumors (5). Yet, despite promising preclinical results, clinical trials have been unimpressive and plagued by adverse events (8-10). This may reflect the poor penetration of therapeutic mAbs to brain, resulting in inadequate target engagement (11). Failures of anti-Aβ immunotherapies to engage with plaques located in deep brain structures may contribute to the lack of translation of these therapies into routine AD treatment (4, 12). Due to the invasiveness and higher degree of complications associated with injections directly to cerebrospinal fluid (CSF), therapeutic antibodies are most commonly administered by intravenous infusion (13-15). However, circulating antibodies have low penetration of the BBB, with only 0.1-0.2% entering brain (16). As a result, therapeutic antibodies are often given at doses 1000-fold greater than the concentration needed to achieve adequate binding of the target antigen in peripheral tissues (1, 17), and these high doses in clinical trials increase the prevalence of adverse events (1, 9, 18) such as amyloid-related imaging abnormalities (ARIA)(19, 20). Thus, there is a need for improved delivery of therapeutic agents to the CNS.

SUMMARY OF INVENTION

This invention addresses the need by providing methods for improving delivery of a composition to the CNS.

In one aspect, the invention provides a method for improving delivery of a composition to a central nervous system interstitium, brain interstitium and/or a spinal cord interstitium of a subject. The method comprises (1) enhancing glymphatic system influx and (2) delivering the composition to the central nervous system interstitium, brain interstitium and/or the spinal cord interstitium. The step of enhancing glymphatic system influx can be carried out in a number of ways. For example, the step can comprise pumping fluid through the central nervous system interstitium, or administering an agent to the subject.

The agent can be a hypertonic solution. In one example, the hypertonic solution is administered into the blood or plasma of the subject. The hypertonic solution can comprise NaCl or mannitol. In other example, the agent can include a Stat-3 inhibitor, a bone morphogenetic protein (BMP) signaling axis molecule, an antagonist of AVP (vasopressin), an antagonist of atrial natriuretic peptide (ANP), an antagonist of Angiotensin II, an antagonist of AT2R receptors, or an antagonist of AT1 receptors.

The composition can be delivered in any suitable ways, such as intracisternally or intrathecally. The composition can be delivered at about the same time or after or before the glymphatic system influx is enhanced. The composition can be an imaging composition or a therapeutic composition. The composition can comprise a small molecule, a virus, a large molecule, a peptide, an antibody, a nucleic acid (e.g., antisense molecules and RNAi agents), or a biologically active fragment thereof. In one example, the therapeutic composition comprises an antibody. The antibody can be conjugated to a ligand that facilitates transport across the blood brain barrier (a.k.a. "BBB"). For example, the ligand can specifically bind to a BBB receptor, (such as transferrin receptor, IGF-R, LDL-R, LRP1, LRP2, and LRP8).

In another aspect, the invention provides a method for treating a neurological disorder in a subject. Examples of the disorder include a neuropathy, an amyloidosis, cancer, an ocular disease or disorder, a viral or microbial infection, inflammation, ischemia, neurodegenerative disease, seizure, behavioral disorder, and lysosomal storage disease. The method comprises (1) enhancing glymphatic system influx and (2) delivering a therapeutic composition to the central nervous system interstitium, brain interstitium and/or the spinal cord interstitium. The step of enhancing glymphatic system influx can be carried out in a number of ways as mentioned above. In one example, the step comprises pumping fluid through the central nervous system interstitium. In another, the step of enhancing glymphatic system influx comprises administering an agent to the subject.

The agent can be a hypertonic solution. In one example, the hypertonic solution is administered into the blood or plasma of the subject. The hypertonic solution can comprise NaCl or mannitol. In other examples, the agent can include a Stat-3 inhibitor, a BMP signaling axis molecule, an antagonist of AVP (vasopressin), an antagonist of ANP, an antagonist of Angiotensin II, an antagonist of AT2R receptors, or an antagonist of AT1 receptors.

The composition can be delivered in any suitable ways, such as intracisternally or intrathecally. The composition can be delivered at about the same time or after or before the glymphatic system influx is enhanced. The composition can comprise a small molecule, a virus, a large molecule, a peptide, an antibody, a nucleic acid (e.g., antisense molecules and RNAi agents), or a biologically active fragment thereof. In one example, the therapeutic composition comprises an antibody. The antibody can be conjugated to a ligand that facilitates transport across the blood brain barrier.

For example, the ligand can specifically bind to a BBB receptor, such as transferrin receptor, IGF-R, LDL-R, LRP1, LRP2, and LRP8.

The antibody can be an anti-Aβ antibody. The subject can be a mammal, such as a human or a non-human primate. In one embodiment, the mammal is a patient in need of treatment, such as an aged or elderly person.

In yet another aspect, the invention features a kit for improving delivery of a composition (e.g., an imaging composition or a therapeutic composition) to the CNS of a subject. The kit comprises the composition and an agent that enhances glymphatic system influx. The agent can be a hypertonic solution, such as a hypertonic solution comprising NaCl or Mannitol. The agent can be a Stat-3 inhibitor, a BMP signaling axis molecule, an antagonist of AVP (vasopressin), an antagonist of ANP, an antagonist of Angiotensin II, an antagonist of AT2R receptors, or an antagonist of AT1 receptors. The composition can comprise a small molecule, a virus, a large molecule, a peptide, an antibody, a nucleic acid, or a biologically active fragment thereof. The antibody can be conjugated to a ligand that facilitates transport across the blood brain barrier. An example of the antibody is an anti-Aβ antibody.

In a further aspect, the invention provides a transcranial macroscopic imaging method. The method comprises introducing an effective amount of an imaging agent to the central nervous system of a subject, and imaging the brain of the subject. The imaging agent can be introduced intracisternally or intrathecally. In a preferred embodiment, the imaging agent comprises a fluorophore and the step of imaging comprises fluorescence macroscopy. In some examples, the fluorophore re-emit light in the infrared region (e.g., the near-infrared region, the mid-infrared region, or the far-infrared region) upon excitation.

The details of one or more embodiments of the invention are set forth in the description below. Other features, objectives, and advantages of the invention will be apparent from the description and from the claims.

BRIEF DESCRIPTION OF THE DRAWINGS

FIGS. 2A, 2B, 2C, 2D, 2E, 2F, 2G. 2H, 2I, and 2J are a set of diagrams and photographs showing that plasma hypertonicity increased CSF influx in anesthetized mice. (A) Fluorescent BSA-647 was delivered into the cisterna magna (CM) of anesthetized mice. Mice received either isotonic saline (KX), hypertonic saline (+HTS), or hypertonic mannitol (+Mannitol) i.p. at the onset of the CM injection. (B) Representative time-lapse images of BSA-647 influx over the immediate 30 minutes following CM injection in the KX, +HTS, and +Mannitol groups. Images (8-bit pixel depth) are color-coded to depict pixel intensity (PI) in arbitrary units (A.U.). Scale bar=2 mm (C) Representative front-tracking analysis of CSF tracer influx over the imaging session for all groups. Fronts are time-coded in minutes. (D) Quantification of the influx area over time (mean±SEM; n=6-7 mice/group; repeated measures two-way ANOVA, Sidak's multiple comparisons test; ****P<0.0001 KX vs.+HTS and +Mannitol). (E) Tracer influx speed maps (μm/min) and (F) quantification of mean influx speeds for all groups (mean±SEM; n=6 mice/group; one-way ANOVA, Tukey's multiple comparisons test; *P<0.05, *P=0.001). (G) Representative ex vivo conventional fluorescence images of intact brains upon removal from the cranium (bottom left; scale bar=2 mm) and after coronal sectioning (top; scale bar=1 mm) from all groups. Coronal sections were imaged with high-powered confocal laser scanning microscopy to evaluate perivascular tracer (bottom right; scale bar=50 μm). (H) Quantification of ex vivo coronal section fluorescence MPI (mean±SEM; n=5-7 mice/group; one-way ANOVA, Tukey's multiple comparisons test; P<0.01, *P=0.003). Total brain uptake of CSF-delivered (I)$^{3}$H-dextran (40 kDa) or (J) $^{14}$C-inulin (6 kDa) in all three groups (mean±SEM; n=5 mice/group; one-way ANOVA, Tukey's multiple comparisons test; P=0.001, *P=0.0009, **P<0.0001). Expressed as percent injected dose (% ID). KX group same as in FIG. 1.

FIGS. 3A, 3B, 3C, 3D, 3E, 3F, 3G, and 3H are a set of diagrams and photographs showing that plasma hypertonicity overrode arousal state inhibition of glymphatic function. (A) Head-plated, awake mice received intracisternal BSA-647. Mice received either isotonic saline (Awake), hypertonic saline (+HTS), or hypertonic mannitol (+Mannitol) i.p. at the onset of the cisterna magna (CM) injection. (B) Representative time-lapse images of BSA-647 influx over the immediate 30 minutes following CM injection in the Awake, +HTS, and +Mannitol groups. Images (8-bit pixel depth) are color-coded to depict pixel intensity (PI) in arbitrary units (A.U.). Scale bar=2 mm Fluorescence was first detected at the base of the brain approximately 5-6 mm below the dorsal cortical surface. (C) Representative front-tracking analysis of CSF tracer influx over the imaging session for all groups. Fronts are time-coded in minutes. (D) Quantification of the influx area over time (mean±SEM;

n=5-7 mice/group; repeated measures two-way ANOVA, Sidak's multiple comparisons test; **P<0.0001 Awake vs.+HTS and +Mannitol). (E) Tracer influx speed maps (μm/min) and (F) quantification of mean influx speeds for all groups (mean±SEM; n=5-7 mice/group; one-way ANOVA, Tukey's multiple comparisons test; P=0.0024, *P=0.0003). (G) Representative ex vivo coronal sections from all groups (scale bar=1 mm). (H) Quantification of ex vivo coronal section fluorescence MPI (mean±SEM; n=5-6 mice/group; one-way ANOVA, Tukey's multiple comparisons test; P=0.0063, ***P=0.003). Awake group same as in FIG. 1.

FIGS. 4A, 4B, 4C, 4D, 4E, 4F, 4G, 4H 4I, 4J, and 4K are a set of diagrams and photographs showing that plasma hypertonicity improved the delivery of an Aβ antibody in 6-month-old APP/PS1 mice and enhanced target engagement. (A)(B) Amyloid plaques were labeled 24 h before with methoxy-X04 (MeX04). Mice were then anesthetized and a fluorescent anti-Aβ antibody was injected intracisternally Mice received either i.p. isotonic saline (Control) or hypertonic saline (+HTS) at the onset of the intracisternal infusion. After 120 min, mice were perfusion-fixed with a fluorescent lectin to label the vasculature. (C) Representative ex vivo images of intact brains upon removal from the cranium (bottom left; scale bar=2 mm) and after coronal sectioning to evaluate antibody penetrance into the brain (top; scale bar=500 mm). Confocal images of the antibody and Aβ plaques (arrows) surrounding the perivascular spaces of penetrating arteries (bottom right; scale bar=100 ittm). (D) Quantification of ex vivo coronal section Aβ antibody fluorescence MPI (mean±SEM; n=5 mice/group; unpaired two-tailed t-test; P=0.0039). (E) Representative high-magnification confocal images of perivascular Aβ plaques (scale bar=20 μm). (F) Percent of target engagement shown by co-labeling of the antibody with MeX04$^+$ Aβ plaques (mean±SEM; n=5 mice/group; unpaired t-test; P=0.005). (G) Nearest neighbor analysis of the average distance of a co-labeled plaque from its nearest perivascular space (PVS) in μm (mean±SEM; total number of co-labeled plaques/number of mice in group; unpaired t-test; ****P<0.0001). (H) Histogram and cumulative frequency plot of the number of co-labeled plaques and distance from the nearest PVS. (I) Representative high-magnification confocal image with orthogonal views showing the anti-Aβ antibody engaging the surface of a plaque (arrows). Scale bar=20 μm. (J) Three-dimensional reconstruction of Aβ plaques from an +HTS-treated mouse showing antibody targeting and engaging plaque surface (scale bar in both=20 μm). (K) Plaque burden was the same between groups (mean±SEM; n=5 mice/group; unpaired t-test; P=0.6165).

Figure 5A:
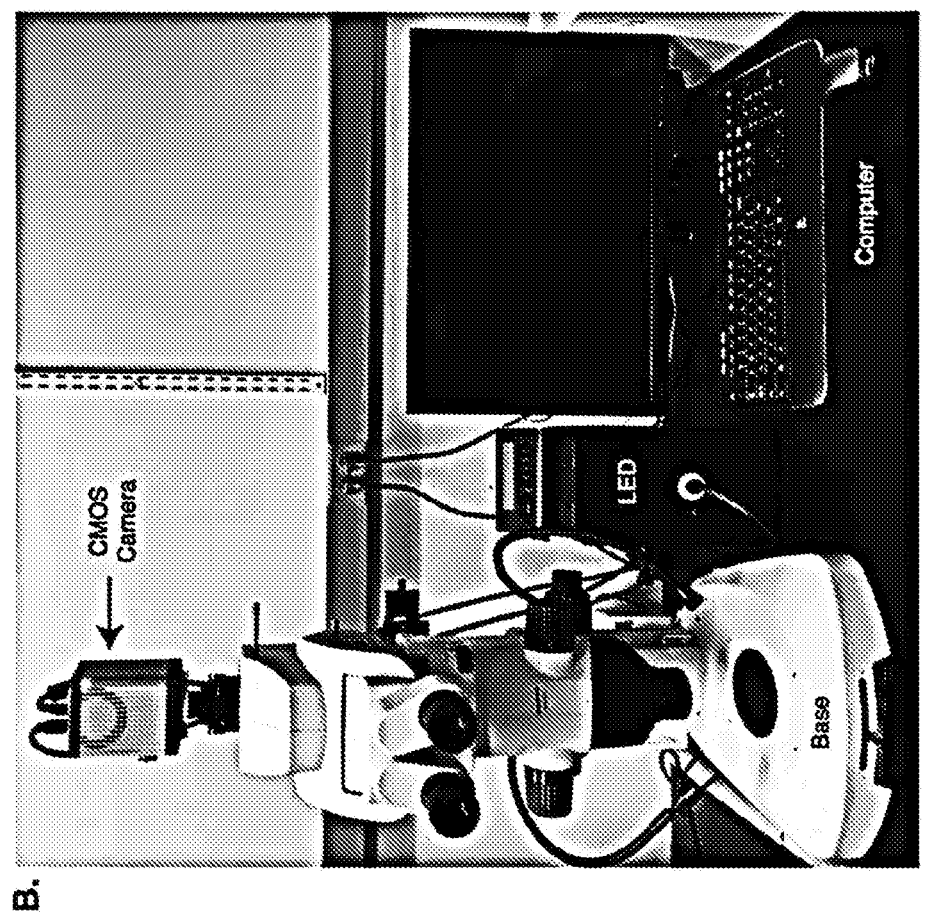
Figure 5B:
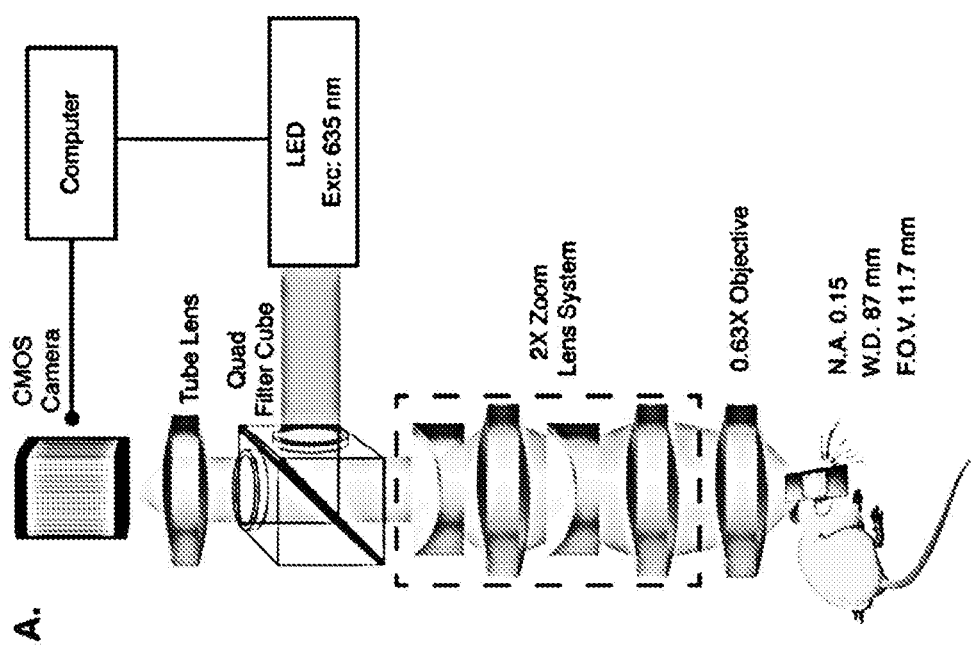
Figures 6A, 6B, 6C, 6D, 6E, 6F, 6G:
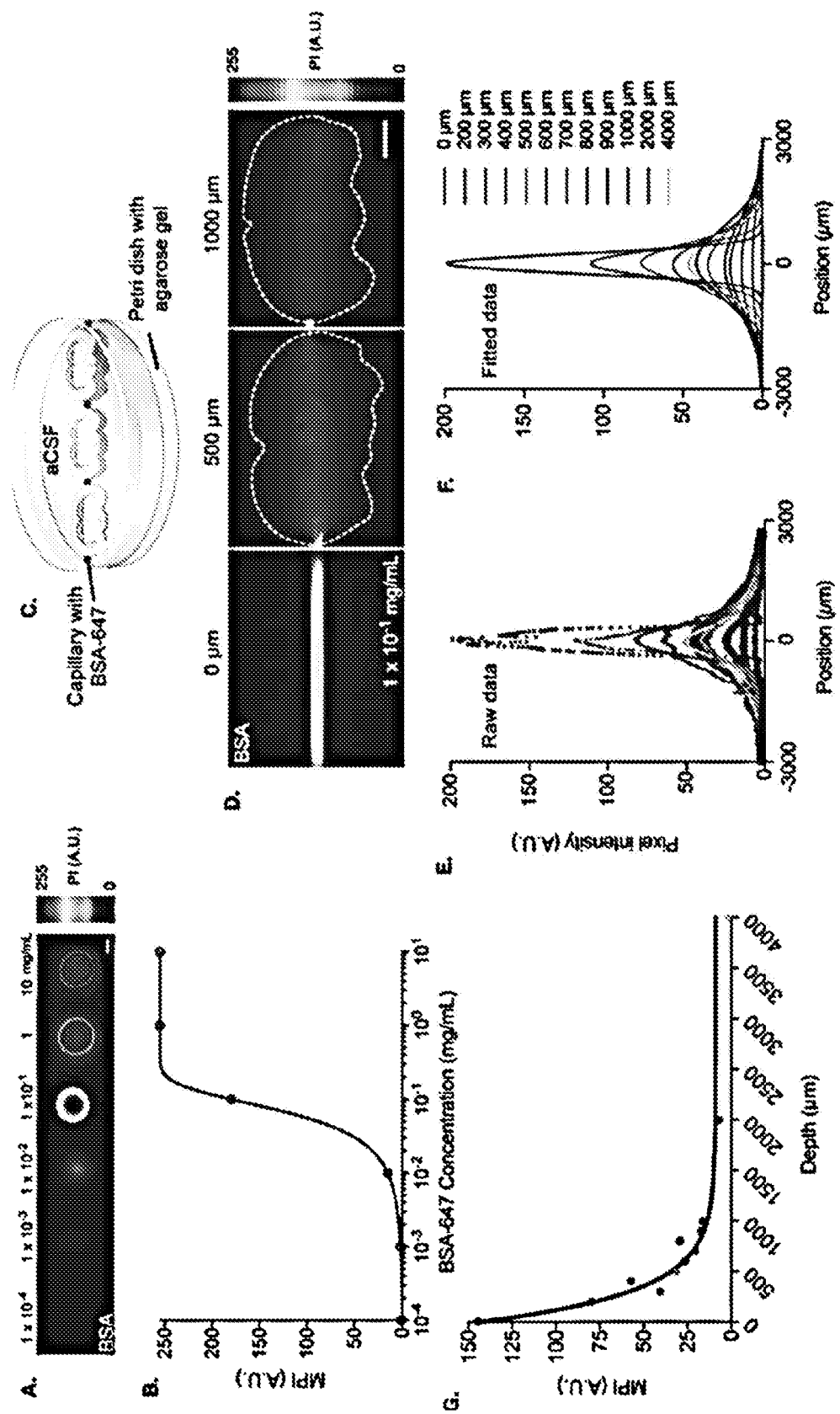

FIGS. 5A and 5B are a set of diagrams and photographs showing a transcranial macroscopic imaging system. (A) Optical schematic. The system uses a tunable LED illumination system that allows individual control of up to 16 different wavelengths. Excitation for 647 nm fluorophores was achieved using a 635 nm wavelength. The imaging software controls rapid switching between wavelengths and when paired with a quad filter cube enables high-speed 4 channel imaging (~100 Hz) without having to rotate the filter turret. The macroscope has a total magnification of 4-40× and with a 0.63× objective permits a long working distance (W.D.) and a high numerical aperture (N.A.) with a field of view (F.O.V.) of about 11.7 mm at the magnification used for this study. This set-up uses a scientific CMOS camera that has an effective area of 13.312×13.312 mm and a full resolution of 2048×2048 pixels, enabling fast image acquisition (100 frames per second). The system is compatible with image splitting optics for simultaneous two-channel applications for dual CSF tracer studies. (B) Photograph of the macroscopic imaging system.

FIGS. 6A, 6B, 6C, 6D, 6E, 6F and 6G are a set of diagrams and photographs showing imaging penetration depth analysis. (A) Bovine serum albumin-conjugated to AlexaFluor 647 (BSA) was serially diluted from 10 to 1×10$^{-4}$ mg/mL in artificial CSF (aCSF). A 10 μl drop was aliquoted into a 96-well plate and imaged on the macroscope at a 635 nm wavelength using the same magnification and exposure time used in the in vivo experiments. Images were color-coded for pixel intensity (PI) in arbitrary units (A.U.) from 0 to 255 (scale bar=2 mm). (B) Mean pixel intensity (MPI) was calculated for each 10 μl droplet and plotted as a function of tracer concentration. The data was fit with a variable slope sigmoidal function. The optimal dilution of tracer that is within the range of the in vivo experiments was 0.1 mg/ml. (C) Schematic of the experimental set-up showing acute coronal sections of increasing thickness placed over a capillary filled with BSA-647 embedded in agar. (D) Representative PI color-coded images of the fluorescent capillary in the plane of focus with: no tissue (0 μm), a 500 μm-thick, and 1,000 μm-thick coronal section placed above the capillary (scale bar=2 mm). (E) Raw PI from 6000 μm line scans centered over the capillary acquired through coronal sections of increasing thickness between 200-4000 μm. (F) Gaussian fit of the raw data from (E) showed good agreement for all ($R^2>0.924$) except the 4,000 μm ($R^2=0.55$). (G) Regions of interest were drawn over the capillary within the perimeter of the coronal section and MPI was measured and plotted as a function of depth. Data was fit using a one phase exponential decay function ($R^2=0.96$) showing that fluorescent signal plateaus between 1-2 mm of tissue thickness, in agreement with results from (F).

FIGS. 7A, 7B, 7C, 7D, 7E, 7F, and 7G are a set of diagrams and photographs showing that in vivo transcranial imaging correlated with tracer transport to the dorsal cortex and ex vivo quantification at all timepoints. Anesthetized mice received cisterna magna (CM) injections of BSA-647 (BSA) during in vivo imaging and brains were extracted and fixed at 5-minute intervals between 5 and 30 minutes after the start of the infusion (n=3 mice/6 time points). (A) Tracer transport color-coded as a function of time after CM injection in sagittal and coronal projections. (B) Coronal sections from the 5, 15, and 30 min time point after CM injection showing that tracer was transported from the base of the brain along the lateral cortical curvature, reaching the dorsal convexity in the later time points (scale bar=2 mm). (C) Mean pixel intensity (MPI) of the last frame from transcranial in vivo imaging correlated with the MPI of 6 coronal sections from the same brain across all 6 time points (Pearson correlation, P=0.0003). (D) MPI has similar kinetics when quantified both in vivo and ex vivo and both data sets have good agreement with a one phase exponential decay function (in vivo: $R^2=0.838$; ex vivo: $R^2=0.834$). (E) To estimate the depth of tracer, MPI in arbitrary units (A.U.) was quantified in 1 mm ROIs starting from the dorsal cortex for all time points. The presence of tracer was determined as MPI values 2 standard deviations above background (dashed line). (F) The estimated distance of tracer below the dorsal cortex after the start of the intracisternal injection. Error bars reflect the 1 mm wide region of interest. Data was also fit with a one phase exponential decay ($R^2=0.976$). (G) In vivo, ex vivo and tracer depth from (D) and (F), respectively, were z-score transformed and fit with a one phase exponential decay function. Extra sum-of-squares F test concluded that all three datasets were fit by a single global model and did not differ significantly (P=0.288; $R^2$=0.913) suggesting that the increase in MPI on transcranial optical imaging is correlated with the tracer moving from the base of the brain towards the dorsal cortex. Data demonstrates that fluorescence is detected as early as 5 min after CM injection, when the bulk of tracer is located 5-6 mm below the cortical surface, providing great sensitivity for whole-brain tracer quantification comparable to terminal ex vivo methods FIGS. 8A, 8B, 8C, 8D, 8E, 8F, and 8G are a set of diagrams and photographs showing that CSF tracer influx seen in transcranial imaging occurred along perivascular spaces surrounding arteries and had similar kinetics to previous in vivo imaging modalities. (A) Macroscopic image from a typical experiment showing brain-wide CSF tracer (BSA-647) influx along the distribution of both middle cerebral arteries (MCA) after intracisternal injection (scale bar=2 mm). (B) To evaluate the anatomical pathway along which CSF inflow occurs, a separate group of mice were imaged through a cranial window using two-photon laser scanning microscopy after intracisternal injection of BSA-Texas Red (TxRd) and i.v. FITC dextran to label vasculature (scale bar=50 μm). The dura mater was left intact and the cranial window was sealed with agarose and a cover slip to prevent intracranial pressure loss. Imaging showed tracer flowing along two perivascular spaces (PVS) on each side of the MCA, below blood vessels of the dura (arrows). (C) Magnified image from inset in (A) shows CSF tracer on each side of the left posterior branch of the MCA (scale bar=500 μm). (D) A line scan from the black line in (C) shows high pixel intensity (PI) in arbitrary units (A.U.) on both sides of the MCA with a decrease in fluorescence over the artery. The width of the space measured in (D) is comparable to that seen in (B). (E) Orthogonal reconstructions from the blue line in (B) shows that CSF tracer is confined to the subpial PVS around the MCA and not within the subarachnoid space (SAS; scale bar=50 μm). (F) Quantification from the mean of 3 perivascular regions of interest along the MCA normalized to the maximum fluorescence intensity ($\Delta F/F_{max}$) of the imaging session expressed as a percent. Higher baseline background fluorescence is seen in 2-P due to bleed through from the vascular label channel. (G) Time to tracer appearance after the start of the intracisternal injections. (mean±SEM; n=4-5 mice/group; ns: not significant; unpaired t-test; P=0.8761).

Figure 9:
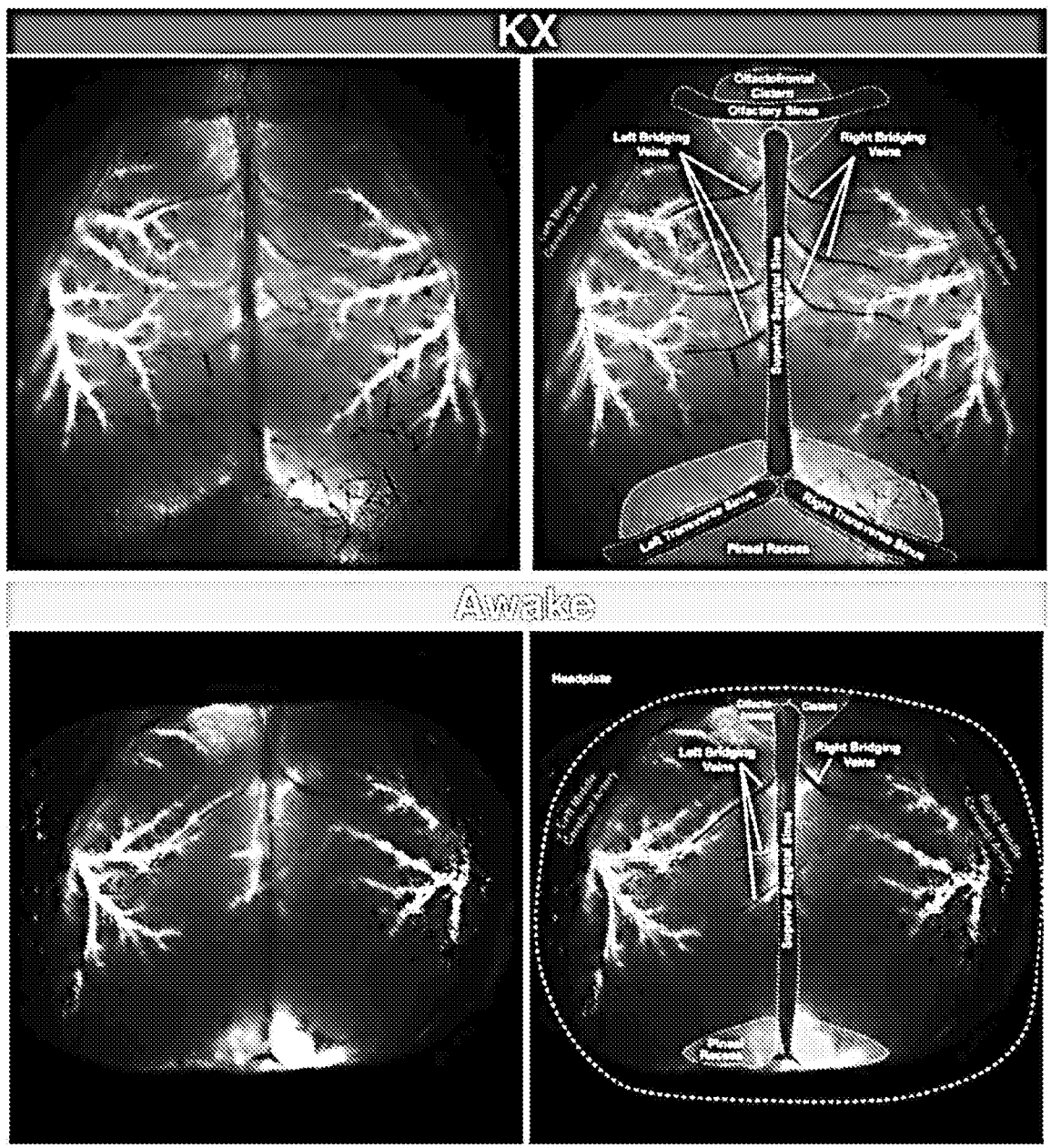

FIG. 9 is a set of photographs showing transcranial macroscopic imaging of CSF influx pathways. After tracer delivery into the cisterna magna it is possible to identify several intracranial structures through the intact skull (dashed line). (Top panel) In anesthetized mice, meningeal structures such as the olfactory sinus, superior sagittal sinus, and the left and right transverse sinuses can be observed (blue). As previously shown, tracer is first found in the large pools of subarachnoid CSF surrounding the brain like those around the olfactofrontal cistern (purple) and the pineal recess (green). Brain uptake of the tracer occurs within the perivascular spaces of pial arteries (red), particularly following the distribution of the anterior and dorsal cortical segments of the middle cerebral artery, and then continues down into the brain along penetrating arteries. Eventually the tracer can be found in the perivenous spaces of the cortical bridging veins and surrounding the meningeal sinuses. (Bottom panel) In awake mice, some of the most anterior and posterior structures are covered by the headplate but all pial perivascular spaces can be readily identified. This approach can also be used for chronic imaging as it is still possible to identify tracer fluxes through transparent dental cement as can be seen on the edges of the headplate.

Figure 10:
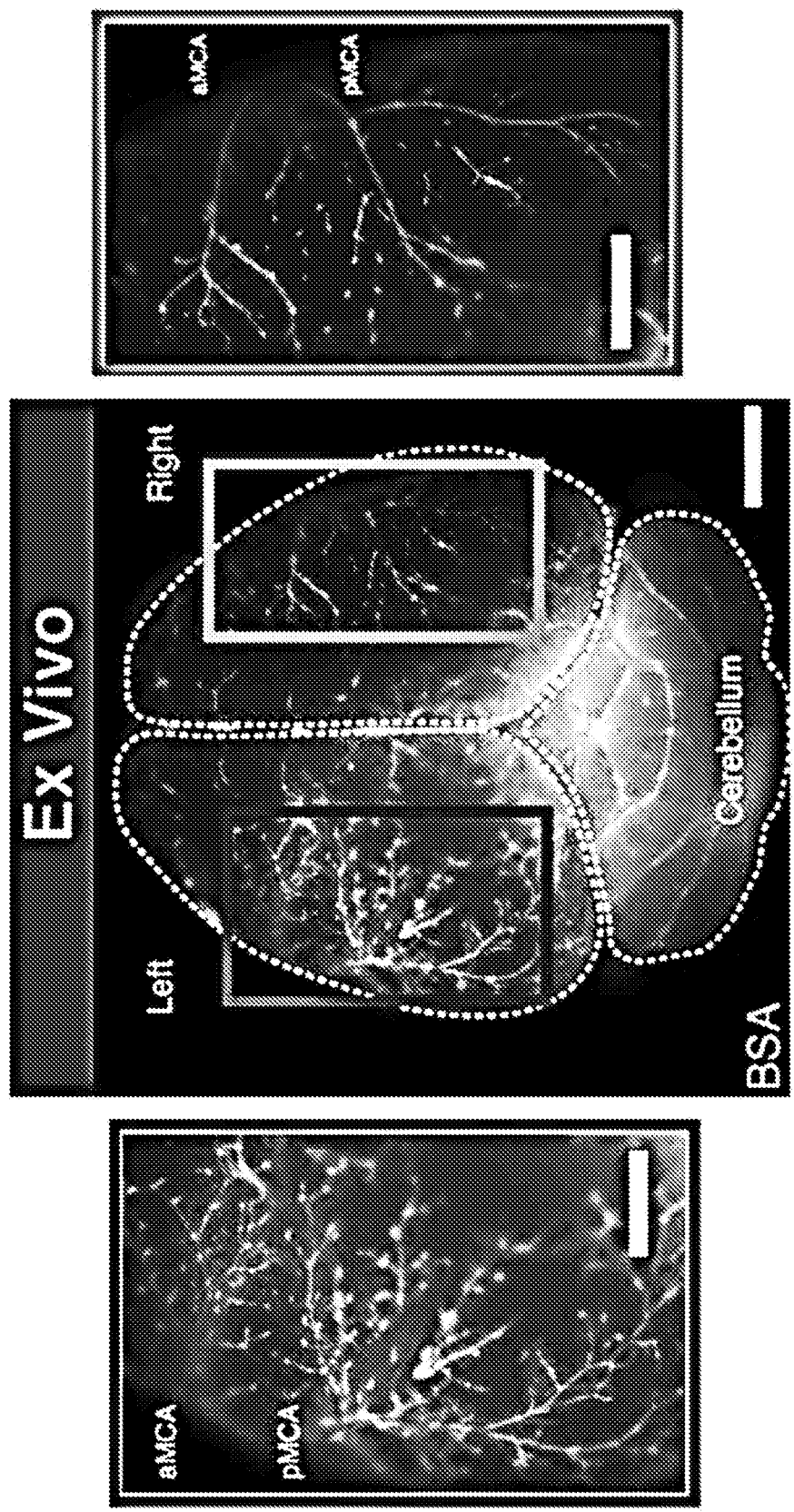

FIG. 10 is a set of photographs showing that CSF tracer inflow routes imaged through the intact skull were also found in the ex vivo brain. (Center) Ex vivo whole brain imaging from an anesthetized mouse, 30 minutes after intracisternal injection (scale bar=2 mm). (Left) Higher magnification insets from the left cortical surface (dark blue) showing that CSF tracers can be found along branches of the anterior middle cerebral artery (aMCA) and posterior MCA (pMCA), traced in red (scale bar=1 mm). (Right) Insets from the right cortex (light blue) demonstrating that tracer influx occurs along the same segments of the aMCA and pMCA (red traces; scale bar=1 mm).

FIGS. 11A, 11B, 11C, 11D, and 11E are a table and a set of diagrams showing inducing plasma hyperosmolarity. (A) Solutions composition and dose used throughout the study. (B) Measured osmolality of plasma tonicity-shifting solutions. (C) Plasma osmolality at 30 minutes after intraperitoneal injection in the control, +HTS, and +Mannitol groups for both the anesthetized (KX) and awake conditions (mean±SEM; n=5-15 mice/group; ordinary two-way ANOVA, Tukey's multiple comparisons test; *P=0.0151, *P=0.0001, P<0.0001). (D) Plasma $Na^+$ ($[Na^+]_{Plasma}$) and (E) $Cl^-$ ($[Cl^-]_{Plasma}$) concentration 30 min after i.p. injection. High $[Na^+]_{Plasma}$ and $[Cl^-]_{Plasma}$ in the +HTS groups account for the hyperosmolarity seen in (c). Mannitol-induced plasma hyperosmolarity does not affect $[Na^+]_{Plasma}$ and $[Cl^-]_{Plasma}$ and is produced by an elevated osmolal gap. (mean±SEM; n=5 mice/group; ordinary two-way ANOVA, Tukey's multiple comparisons test; *P<0.001, ****P<0.0001).

FIGS. 12A, 12B, and 12C are a set of diagrams and photographs showing that Manipulations of plasma tonicity did not disrupt the blood-brain barrier. (A) Representative ex vivo coronal section images of FITC-dextran (1% m/v, 70 kDa) extravasation 30 minutes following intraperitoneal isotonic saline (KX), hypertonic saline (+HTS), and hypertonic mannitol (+Mannitol) solution administration in anesthetized animals. Positive controls received intracarotid 2M mannitol (+IC Mannitol). (scale bar=1 mm). (B) Quantification of thresholded fluorescence expressed as percent area from 6 coronal sections depicted in (A) revealed no significant increases in extravasated FITC-dextran between the experimental groups but did show a significant difference between the experimental groups and the positive control, (mean±SEM; n=5-6 mice/group; one-way ANOVA, Tukey's multiple comparisons test, ns: not significant, P>0.999; ***P<0.0002). (C) Plasma concentration of the FITC-dextran was evaluated spectrophotometrically and revealed no significant differences between any of the experimental groups but did show increased extravasation of the dextran in the positive control group (mean±SEM; n=5-6 mice/group; one-way ANOVA, Tukey's multiple comparisons test, *P=0.0426).

Figures 13A, 13B:
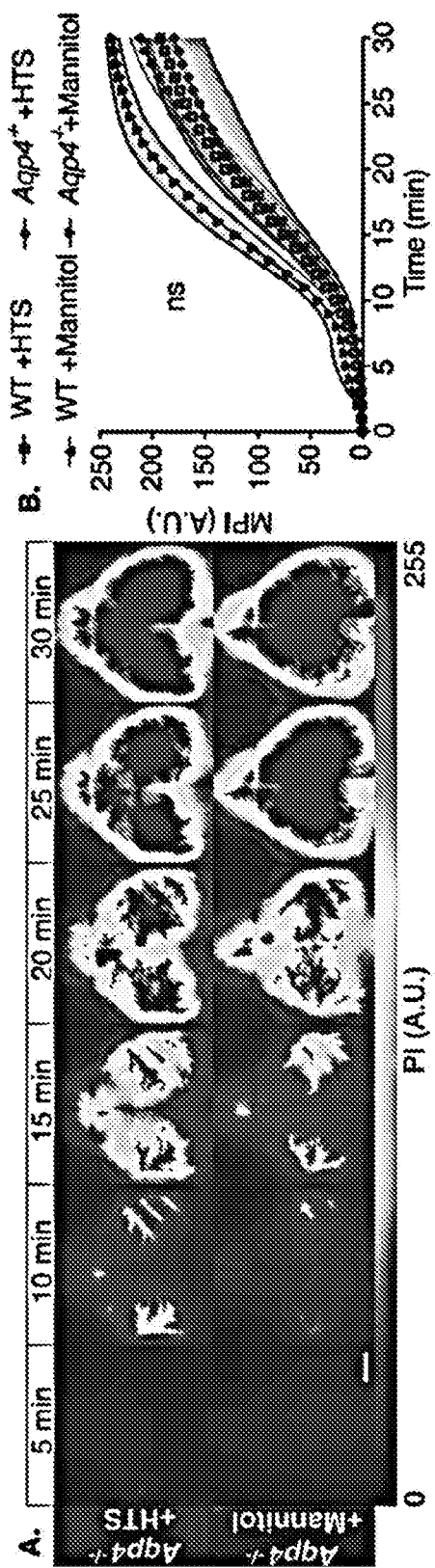

FIGS. 13A and 13B are a set of photographs and a diagram showing that plasma hypertonicity overrode glymphatic inhibition in $Aqp4^{-/-}$ mice. Fluorescent BSA-647 was delivered into the cisterna magna (CM) of anesthetized $Aqp4^{-/-}$ mice. Mice received either hypertonic saline ($Aqp4^{-/-}$+HTS), or hypertonic mannitol ($Aqp4^{-/-}$+Mannitol) i.p. at the onset of the CM injection. (A) Representative time-lapse images of BSA-647 influx over the immediate 30 minutes following CM injection in the $Aqp4^{-/-}$+HTS, and $Aqp4^{-/-}$+Mannitol groups. Images (8-bit pixel depth, 0-255) are color-coded to depict pixel intensity (PI) in arbitrary units (A.U.). Scale bar=2 mm (B) Quantification of the mean pixel intensity (MPI) over time compared to the wild type groups from FIG. 2 (WT+HTS, WT+Mannitol; mean±SEM; n=3-5 mice/group; repeated measures two-way ANOVA, Sidak's multiple comparisons test; group effect: P=0.1029; ns: not significant).

FIGS. 14A, 14B, 14C, and 14D are a set of diagrams and photographs showing that in vivo transcranial imaging correlated with ex vivo quantification of fluorescent and radiolabeled tracers. (A) Images acquired at 30 min after in vivo imaging were analyzed for mean pixel intensity (MPI; purple) and influx area using front-tracking software (green). Mice were fixed and images of the dorsal whole brain (blue) and coronal sections (red) were acquired from the same brain using the macroscope. (B) Z-scores were calculated for all outcomes and a multiple linear regression model was generated from the data and plotted with 95% confidence intervals. All metrics had a significant positive linear relationship and were strongly correlated with ex vivo coronal sections (Whole Brain: $R^2=0.8473$; In vivo MPI: $R^2=0.7354$; In vivo Influx Area: $R^2=0.8355$). The slopes of all three regressions were not significantly different from each other (P=0.8209). Fluorescent tracer quantification from (C) ex vivo coronal sections and (D) in vivo imaging (influx area) was also tightly correlated with quantification of two separate radiotracers: $^3$H-dextran (40 kDa) and $^{14}$C-inulin (6 kDa) using plasma osmolality as the predictor (Coronal sections: $R^2=0.589$; In vivo: $R^2=0.8072$; $^3$H-Dextran: $R^2=0.6832$; $^{14}$C-Inulin: $R^2=0.6973$). The overall slopes of all regressions were not significantly different (P>0.05).

FIGS. 15A, 15B, 15C, and 15D are a set of diagrams showing that plasma hyperosmolarity caused a decrease in intracranial pressure and interstitial fluid volume without altering mean arterial blood pressure or cerebral blood flow. (A) Mean arterial blood pressure (MAP) in the femoral artery of anesthetized mice (KX) was recorded in mmHg, starting 5 min before i.p. injection of isotonic saline (Control), hypertonic saline (+HTS), and hypertonic mannitol solution (+Mannitol), for 30 minutes (mean±SEM n=4-5 mice/group; repeated measures two-way ANOVA, Tukey's multiple comparisons test; P<0.01, color-coded asterisks denote a difference between KX and +HTS or KX and +Mannitol at different time points). (B) Relative cerebral blood flow (rCBF; pressure units, p.U.) was measured using laser Doppler flowmetry (mean±SEM; n=3-5 mice/group; repeated measures two-way ANOVA, Tukey's multiple comparisons test; P<0.01, color-coded asterisks denote a difference between KX and +Mannitol at different time points). (C) Intracranial pressure (ICP) recording for the 5 minutes prior to and 30 minutes following i.p. injection at 0 minutes (mean±SEM; n=4-5 mice/group; repeated measures two-way ANOVA, Tukey's multiple comparisons test; **P<0.0001). (D) Brain water content at 30 minutes following i.p. injection in the control and hypertonic groups (mean±SEM; n=4-10 mice/group; ordinary two-way ANOVA, Tukey's multiple comparisons test; *P=0.0001, ****P<0.0001).

Figure 16:
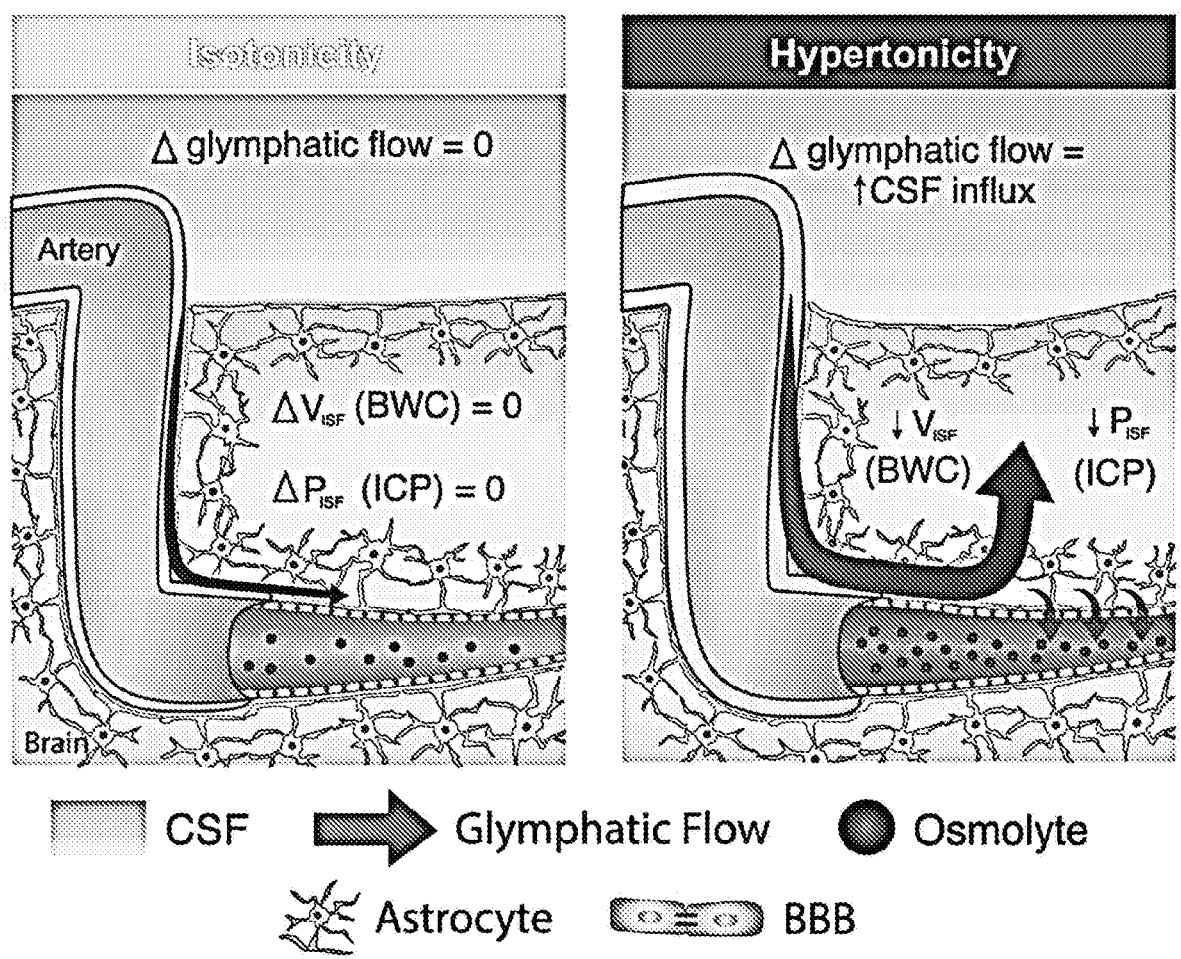

FIG. 16 is a set of diagrams showing a three-compartment model of the relationship between blood plasma, brain, and CSF under isotonic and hypertonic conditions. In the situation of an isotonic blood plasma, there is no change in interstitial fluid volume (VIsF; brain water content, BWC) or pressure (PIsF; intracranial pressure, ICP), and as a result there is no change in the net direction or magnitude of glymphatic flow. In the hypertonic condition, with increased plasma osmolyte content there will be a net resorption of ISF, resulting in decreased ISF volume, and a negative ISF pressure that will enhance CSF influx into brain.

Figure 17:
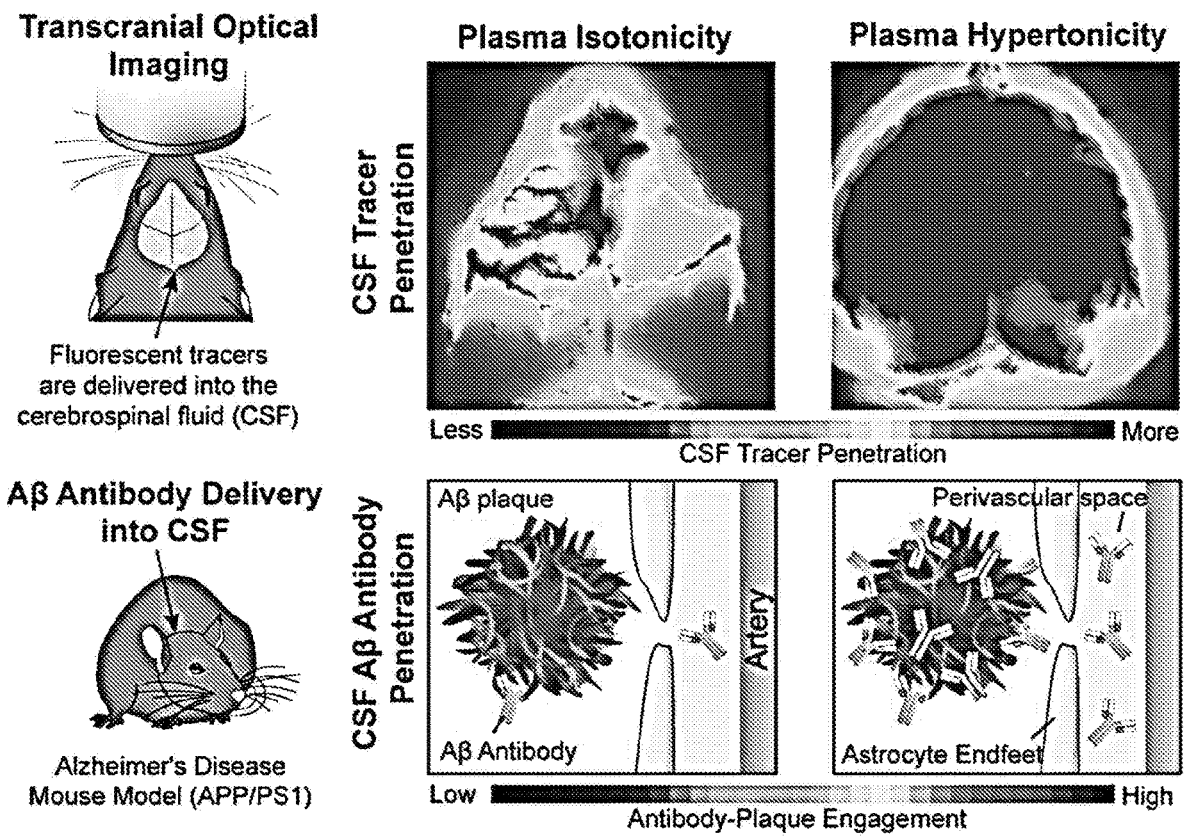

FIG. 17 is a set of diagrams and photographs showing transcranial optical imaging and Aβ antibody delivery into CSF (left panel) and CSF tracers and Aβ antibody under isotonic and hypertonic conditions (right panel).

DETAILED DESCRIPTION OF THE INVENTION

Despite the initial promise of immunotherapy for CNS disease, multiple recent clinical trials have failed. This may be due in part to characteristically low penetration of antibodies to cerebrospinal fluid (CSF) and brain parenchyma, resulting in poor target engagement. There is a need for improved delivery of therapeutic antibodies as well as other agents to the CNS.

This invention discloses utilizing novel transcranial macroscopic imaging to non-invasively evaluate in vivo delivery pathways of CSF fluorescent tracers. Tracers in CSF proved to be distributed through a brain-wide network of periarterial spaces, denoted as the glymphatic system. Unexpectedly, it was found that CSF tracer entry could be enhanced substantially by increasing plasma osmolality without disruption of the blood-brain barrier. Further, it was unexpected that plasma hyperosmolality overrode the inhibition of glymphatic transport that characterizes the awake state and reversed glymphatic suppression in a mouse model of Alzheimer's disease. As disclosed herein, plasma hyperosmolality enhanced the delivery of an amyloid-β (Aβ) antibody, obtaining a 5-fold increase in antibody binding to Aβ plaques. Thus, manipulation of glymphatic activity represents a novel strategy for improving penetration of therapeutic agents such as antibodies to the CNS.

A bulk flow pathway exists along the perivascular space (PVS) surrounding the pial and penetrating arteries for CSF circulation into the brain (21-25). Although antibodies show limited diffusive transport in the CNS extracellular space (26, 27), harnessing perivascular and parenchymal convective flows can enhance their delivery into the brain. This bulk flow pathway, termed the glymphatic system for its role in solute clearance and its dependence on the glial water channel aquaporin-4 (AQP4) (21), represents an ideal mechanism for drug delivery to the CNS. The fast, convective fluid flow within the glymphatic system effectively delivers solutes of high molecular weight (21) but is strongly regulated by brain state (28), aging (29), arterial pulsatility (30), and body posture (31).

This invention provides a novel non-invasive transcranial macroscopic imaging approach that allows one to track cortical CSF flow in real time in the intact brain of living mice. In this invention, this technique was used to evaluate if therapeutic enhancement of glymphatic influx would increase the delivery of CSF-based tracers into the brain. It was unexpectedly found that increasing plasma osmolality with a hypertonic solution, such as hypertonic saline or mannitol, increased glymphatic influx without disruption of the BBB. Disclosed herein is the first study describing the use of non-invasive transcranial macroscopic imaging to evaluate CSF flow patterns in rodents. As disclosed in the working examples below, inventors observed advective tracer inflow within the leptomeningeal PVS surrounding large cerebral arteries, which matched findings in previously validated radiometric and fluorescent ex vivo quantification methods (21). Moreover, macroscopic imaging corroborated prior findings in relation to arousal state and AQP4 expression (21). Importantly, it was demonstrated that hyperosmolar therapy with e.g., intraperitoneal hypertonic saline or mannitol, doubled the penetration of an intracisternally-delivered CSF tracer, while increasing influx speeds by about 70%. This response is attributed to an increase in ISF-to-plasma efflux, causing a decrease in ICP without BBB disruption (FIG. 16). Although controlled opening of the BBB, allowing greater entry of drugs from blood to the CNS, has shown promissory results in improving drug delivery; the effect of this intervention on brain function and glymphatic clearance are yet unknown, requiring further evaluation. This intervention overcame the suppression of CSF inflow that characterizes the awake state, AQP4 depletion, and the diseased AD brain (28, 35). More specifically, plasma hypertonicity sharply improved delivery of fluorophore-conjugated Aβ antibody. Brain-wide distribution of the antibody resulted in significantly higher plaque engagement, with targeted plaques lying distinctly farther from the PVS despite a short CSF circulation time. Hyperosmolar therapy with intravenous hypertonic solutions is already clinically approved for the treatment of cerebral edema (49). Hyperosmolar therapy should enhance immunotherapy delivery deep within the brain parenchyma. Although antibodies are large molecules, proteins as large as 2,000 kDa can enter the brain parenchyma after intracisternal delivery (21, 26). Indeed, under pathological conditions such as AD, antibodies (>100 kDa) are transported through the PVS (27). Since this transport is primarily mediated by bulk flow, transport of smaller molecules can also be likewise enhanced.

The study disclosed herein shows that plasma hypertonicity can rescue impaired glymphatic function in a murine AD model, enhancing the delivery and target engagement of passive immunotherapeutics against A13. The study also show that one can use substantially less antibody than required in previous studies, while achieving greater target engagement (27, 58). As disclosed herein, exploiting hyperosmotic treatment to overcome the declining glymphatic flux in the awake state, in aging, and in disease can be combined with convection enhanced delivery strategies.

Plasma Hyperosmolality and Increased CSF Influx

The present invention provides a method for improving delivery of a composition to a central nervous system interstitium, brain interstitium and/or a spinal cord interstitium of a subject comprising. The method includes enhancing glymphatic system influx and delivering the composition to the central nervous system interstitium, brain interstitium and/or the spinal cord interstitium.

One can enhance glymphatic system influx via a number of ways. For example, one can pump fluid through the central nervous system interstitium using methods and agents known in the art such as those described in WO2014130777. For instance, enhancing glymphatic system influx can comprise a step of administering an agent to a subject (such as a mammal) that increases glymphatic clearance, e.g., a Stat-3 inhibitor or BMP signaling axis molecules. In other embodiments, the agent is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD12331 9, or an antagonist of AT1 receptors such as valsartan. In another embodiment, the agent is an agent for use in the treatment of insomnia or as an aid for sleep, including but not limited to those listed below:

| Types of agent | Examples |
| --- | --- |
| Antihistamines | ALLEGRA ® (Fexofenadine), BENADRYL ® (Diphenhydramine), CLARITIN ® or TAVIST ® (loratadine), CHLOR-T RIM ETON ® (chlorphenir amine maleate), DIMETANE ® (Brompheniramine, Phenylpropanolamine), and ZYRTEC ® (Cetirizine) |
| Nonprescription sleep aids | Unisom Nighttime Sleep-Aid, Dormin, Nytol, Simply Sleep, Sominex, Extra Strength Tylenol PM, Diphenhydramine hydrochloride, and Excedrin P.M. |
| Benzodiazepines: | PROSUM ® (estazolam), DALMANE ® (flurazepam), DORAL ® (quazepam), RESTORIL ® (temazepam), HALCION ® (triazolam), and VALIUM ® (diazepam) |
| Non-benzodiazepines: | Imidazopyriclines: AMBIEN ®, AMBIEN ® CR, INTERMEZZO ® (Zolpidem) (class of its own), and SONATA ® (pyrazolopyrimicline) (class of its own) Melatonin receptor stimulator: ROZEREM ® (ramelteon), NOTED ® (chloral hydrate), PRECEDEX ® (dexmedetomidine hydrochloride), and LUNESTA ® (eszopiclone) |
| Barbiturates | NEMBUTAL ® (phenobarbital), MEBARAL ® (mephobarbital) , and Amytal Sodium (amobarbital sodium), BUTISOL ® (butabarbital sodium), and SECONAL ® Sodium Pulvules (secobarbital sodium) |

In another embodiment, the agent can be an agent that prevents AQP4 depolarization or loss of AQP4 polarization, such as JNJ-1 7299425 or JNJ-17306861. In another embodiment, the step of increasing glymphatic influx comprises the step of pumping fluid through the central nervous system interstitium. Pumping can be accomplished by any device or method known in the art, for example, by using a mechanical pump, an infusion pump, etc.

Alternatively, the step of enhancing glymphatic system influx comprises administering a hypertonic agent to the subject. Preferably, the hypertonic agent is a hypertonic solution, which can be administered into plasma of the subject.

Each of the agents described above can be used alone or in combination with one or more of the other agents.

As used herein, "hypertonic" and "hypotonic" are relative terms e.g., in relation to physiological osmolality, but can diverge from this so long as the ultimate goal of an osmotic differential or gradient is achieved between two compartments (such as the blood plasma and the central nervous system interstitium) so as to promote the influx of glymphatic flow into central nervous system interstitium, brain interstitium and/or a spinal cord interstitium. Accordingly, a "hypertonic solution" refers any physiologically and/or pharmaceutically acceptable solution that is hypertonic with respect to physiological osmolality, including hypertonic saline or sugar solutions. As mentioned herein, hypertonic solutions preferred in this invention does not cause BBB disruption.

The methods of the invention provide an agent (e.g., a pharmaceutical preparation) for injection that is hypertonic with respect to blood. To determine whether a pharmaceutical preparation is hypertonic with respect to blood, one calculates the osmolarity for all chemical components of a solution including the diluent. Tonicity can be calculated for fluids and dissolved or diluted medications, which are expressed in a numerical value of milliosmoles per liter of fluid (mOsm/L) or per kilogram of solvent (mOsm/kg). These two values also known as osmolarity and osmolality, respectively. The osmolarity of blood ranges between 285 and 310 mOsm/L and the osmolality of blood ranges between 275 and 299 mOsm/kg.

Solution osmolarity is based in part on the concepts of osmosis and osmotic pressure. Osmosis is the diffusion of solutes (dissolved particles) or the transfer of fluid through semipermeable membranes such as blood vessels or cell membranes. Osmotic pressure, which facilitates the transport of molecules across membranes, is expressed in osmolar concentrations and is referred to as hypo-osmotic (hypotonic), iso-osmotic (isotonic), or hyper-osmotic (hypertonic) when compared with biologic fluids such as blood or plasma. The term "tonicity" and "osmotic pressure" are often considered synonymous.

The osmotic pressure is the hydrostatic (or hydraulic) pressure required to oppose the movement of water through a semipermeable membrane in response to an 'osmotic gradient' (i.e., differing particle concentrations on the two sides of the membrane). Serum osmolality can be measured by use of an osmometer (see Example 3 below) or it can be calculated as the sum of the concentrations of the solutes present in the solution.

As used herein, tonicity and osmotic pressure are to be considered synonymously, and are to be understood broadly. Tonicity can mean the effective osmolality and is equal to the sum of the concentrations of the solutes in a solution that have the capacity to exert an osmotic force across a membrane, including a cell membrane. In the strict sense, osmolality is a property of a particular solution and is independent of any membrane. Tonicity is a property of a solution in reference to a particular membrane. However, the invention shall refer to solutions being isotonic, hypertonic, or hypotonic with respect to biological solutions such as blood or plasma, and this referencing shall include the meaning that the particular solution is isotonic hypertonic, or hypotonic with blood or plasma with respect to a cell membrane of a cell in the blood or plasma or other biological solution.

An operational definition of tonicity can be used to explain the term. This can be based on an experiment of adding a test solution to whole blood and observing the result. If the RBCs in whole blood swell and rupture, the test solution is said to be hypotonic compared to normal plasma. If the RBCs shrink and become crenate, the test solution is said to be hypertonic compared to normal plasma. If the RBCs stay the same, the test solution is said to be isotonic with plasma. The RBC cell membrane can be the reference membrane. For example, whole blood placed in normal saline (i.e., 0.9% sodium chloride) will not swell, and hence normal saline is said to be isotonic.

The methods described herein include administering to a subject a pharmaceutical solution or preparation that is hypertonic with respect to plasma or blood. As hypertonic solutions, once injected into blood, may cause fluid shifts out of cells and a variety of negative effects, care should be taken to select a proper osmolality that are not so hypertonic as to cause significant thrombosis and/or vessel irritation. In one embodiment, the solution/preparation is considered to have suitable osmolality if 30 minute after injection into a subject in the manner described in the working example below, the resulting plasma osmolality is greater than about 320 mOsml.kg$^{-1}$ and less than about 600 mOsml.kg$^{-1}$, e.g., greater than about 340 or 350 and less than about 375, 400, 425, 450, 475, 500, or about 575 mOsml.kg$^{-1}$. In general, hypertonic solutions useful in this invention exhibit a tonicity that is greater than about 320 mOsml.kg$^{-1}$, e.g., 340 to 3,000 (e.g., 500 to 2,000, 1,000 to 2,000, 1,500 to 1,800) mOsml.kg$^{-1}$. Solutions with an osmolality that is greater than about 600 mOsml.kg$^{-1}$ should be used with care in injections.

Various primary bulking agents can be used for preparing a hypertonic solution/preparation for intravenous injection. Examples include ionizing agents, e.g., NaCl, and non-ionizing. Examples of non-ionizing bulking agents include, but are not limited to, mannitol, glycine, sucrose, lactose, other disaccharides, therapeutic proteins or the active ingredient of a formulation itself, or other bulking agents known to one skilled in the art. The concentrations of non-ionizing bulking agents do not significantly affect whether a solution has a sufficient ionic strength. However, their concentrations do have an effect on osmolarity, and therefore, their concentrations can have an effect on tonicity. In certain examples, NaCl or mannitol is used. The osmotic diuretic mannitol or hypertonic saline can establish an osmotic gradient between plasma and brain cells and draws water across the BBB into the vascular compartment. Exemplary dosages for mice were described in the working examples below. The human equivalent doses (HED) can be obtained using methods known in the art. See e.g., Nair A B, Jacob S. J Basic Clin Pharm. 2016 March;7(2):27-31. doi: 10.4103/0976-0105.177703 and the FDA's Guidance for Industry. Estimating the Maximum Safe Starting Dose in Initial Clinical Trials for Therapeutics in Adult Healthy. For example, to a human subject, NaCl may be administered at 30 mg/kg or more (e.g., 30 to 300 mg/kg) and mannitol may be administered at 130 mg/kg or more (e.g., 130 to 1300 mg/kg).

FIG. 16 shows a three-compartment model of the relationship between blood plasma, brain, and CSF under isotonic and hypertonic conditions. In the situation of an isotonic blood plasma, there is no change in interstitial fluid volume (VIsF; brain water content, BWC) or pressure (PIsF; intracranial pressure, ICP), and as a result there is no change in the net direction or magnitude of glymphatic flow. In the hypertonic condition, with increased plasma osmolyte content there will be a net resorption of ISF, resulting in decreased ISF volume, and a negative ISF pressure that will enhance CSF influx into brain.

In fact, as shown in the examples below, hyperosmolar therapy with e.g., intraperitoneal hypertonic saline or mannitol, doubled the penetration of an intracisternally-delivered CSF tracer, while increasing influx speeds by about 70%. This response is attributed to an increase in ISF-to-plasma efflux, causing a decrease in ICP without BBB disruption. Accordingly, the same approach can be used to improve the delivery of any composition or compound of interest into the CNS interstitium.

In some embodiments, a composition or compound to be delivered (e.g., therapeutic composition or an imaging composition) is administered intracisternally or intrathecally. Other routes of administration (e.g., parenteral delivery, intravenous delivery, intradermal, or intramuscular intramuscular) can also be used. In that case, the composition or compound will need to cross the BBB. In that case, various means known in the art can be used to facilitate BBB crossing. See, e.g., U.S. Pat. Nos. 9,675,849, 7,943,129, US20180134797, US20180237496, and US 20170145076.

For example, the composition or compound can be modified, linked, or conjugated with polypeptides that bind to a BBB receptor and are capable of being transported across the BBB. BBB receptors are expressed on BBB endothelia, as well as other cell and tissue types. Binding of a polypeptide to the BBB receptor can initiate internalization of the polypeptide and transport across the BBB. Such receptors include, but are not limited to, TMEM30A, transferrin receptor (TfR), insulin receptor, insulin-like growth factor receptor (IGF-R), low density lipoprotein receptor (LDLR), low density lipoprotein receptor-related protein 1 (LRP1), low density lipoprotein receptor-related protein 2 (LRP2), low density lipoprotein receptor-related protein 8 (LRP8), GLUT1, basigin, diphtheria toxin receptor, membrane-bound precursor of heparin binding epidermal growth factor-like growth factor (HB-EGF), melanotransferrin, and vasopressin receptor.

In the case where the compound is an antibody, certain domains of the antibody (e.g., the Fc region or one of the antigen-binding domain) can be modified to generate a mutant Fc region or a bi-specific antibody capable of binding to a blood-brain barrier receptor. U.S. Pat. No. 9,676,849, US20180134797, and US20180237496.

Non-polypeptide compounds may also be joined to a BBB receptor-binding polypeptide. Such agents include cytotoxic agents, imaging agents, DNA or RNA molecules, or small molecule compounds. In some embodiments, the compound is a small molecule, e.g., less than 1000 Da, less than 750 Da, or less than 500 Da.

A compound, either a polypeptide or non-polypeptide, may be joined to the N-terminal or C-terminal region of the BBB receptor-binding polypeptide, or attached to any region of the polypeptide, so long as the compound does not interfere with binding of the BBB-receptor binding polypeptide to the BBB receptor. In various embodiments, the conjugates can be generated using well-known chemical cross-linking reagents and protocols. For example, there are a large number of chemical cross-linking agents that are known to those skilled in the art and useful for cross-linking the polypeptide with a compound of interest.

Therapeutic Methods

The hyperosmolality-mediated CSF influx described above may be used in therapeutic methods. In some aspects, the invention provides a method of transporting a therapeutic composition or compound into CNS of a patient or subject. The patient or subject can be one having a neurological disorder, including, without limitation: Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, traumatic brain injury, etc.

In some embodiments, the neurological disorder is selected from: a neuropathy, an amyloidosis, cancer (e.g. involving the CNS or brain), an ocular disease or disorder, a viral or microbial infection, inflammation (e.g. of the CNS or brain), ischemia, neurodegenerative disease, seizure, behavioral disorder, lysosomal storage disease, etc. The methods of the invention are particularly suited to treatment of such neurological disorders due to their ability to transport one or more associated active ingredients or therapeutic compounds into the CNS/brain where such disorders find their molecular, cellular, or viral/microbial basis.

Neuropathy disorders are diseases or abnormalities of the nervous system characterized by inappropriate or uncontrolled nerve signaling or lack thereof, and include, but are not limited to, chronic pain (including nociceptive pain), pain caused by an injury to body tissues, including cancer-related pain, neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea.

For a neuropathy disorder, a neurological drug may be selected that is an analgesic including, but not limited to, a narcotic/opioid analgesic (i.e., morphine, fentanyl, hydrocodone, meperidine, methadone, oxymorphone, pentazocine, propoxyphene, tramadol, codeine and oxycodone), a non-steroidal anti-inflammatory drug (NSAID) (i.e., ibuprofen, naproxen, diclofenac, diflunisal, etodolac, fenoprofen, flurbiprofen, indomethacin, ketorolac, mefenamic acid, meloxicam, nabumetone, oxaprozin, piroxicam, sulindac, and tolmetin), a corticosteroid (i.e., cortisone, prednisone, prednisolone, dexamethasone, methylprednisolone and triamcinolone), an anti-migraine agent (i.e., sumatriptin, almotriptan, frovatriptan, sumatriptan, rizatriptan, eletriptan, zolmitriptan, dihydroergotamine, eletriptan and ergotamine), acetaminophen, a salicylate (i.e., aspirin, choline salicylate, magnesium salicylate, diflunisal, and salsalate), an anti-convulsant (i.e., carbamazepine, clonazepam, gabapentin, lamotrigine, pregabalin, tiagabine, and topiramate), an anaesthetic (i.e., isoflurane, trichloroethylene, halothane, sevoflurane, benzocaine, chloroprocaine, cocaine, cyclomethycaine, dimethocaine, propoxycaine, procaine, novocaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin), and a cox-2-inhibitor (i.e., celecoxib, rofecoxib, and valdecoxib). For a neuropathy disorder with vertigo involvement, a neurological drug may be selected that is an anti-vertigo agent including, but not limited to, meclizine, diphenhydramine, promethazine and diazepam. For a neuropathy disorder with nausea involvement, a neurological drug may be selected that is an anti-nausea agent including, but not limited to, promethazine, chlorpromazine, prochlorperazine, trimethobenzamide, and metoclopramide.

Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract).

For amyloidosis, a neurological drug may be selected that includes, but is not limited to, an antibody or other binding molecule (including, but not limited to a small molecule, a peptide, an aptamer, or other protein binder) that specifically binds to a target selected from: beta secretase, tau, presenilin, amyloid precursor protein or portions thereof, amyloid beta peptide or oligomers or fibrils thereof, death receptor 6 (DR6), receptor for advanced glycation endproducts (RAGE), parkin, and huntingtin; a cholinesterase inhibitor (i.e., galantamine, donepezil, rivastigmine and tacrine); an NMDA receptor antagonist (i.e., memantine), a monoamine depletor (i.e., tetrabenazine); an ergoloid mesylate; an anti-cholinergic antiparkinsonism agent (i.e., procyclidine, diphenhydramine, trihexylphenidyl, benztropine, biperiden and trihexyphenidyl); a dopaminergic antiparkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homotaurine (i.e., 3-aminopropanesulfonic acid; 3APS); a serotonin receptor activity modulator (i.e., xaliproden); an, an interferon, and a glucocorticoid.

Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors. For cancer, a neurological drug may be selected that is a chemotherapeutic agent.

Examples of chemotherapeutic agents include alkylating agents such as thiotepa and CYTOXANO cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphor-amide and trimethylolomelamine; acetogenins (especially bullatacin and bullatacinone); delta-9-tetrahydrocannabinol (dronabinol, MARINOL); beta-lapachone; lapachol; colchicines; betulinic acid; a camptothecin (including the synthetic analogue topotecan (HYCAMTIN), CPT-11 (irinotecan, CAMPTOSAR), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN. doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK. polysaccharide complex (JHS Natural Products, Eugene, OR); razoxane; rhizoxin; sizofiran; spirogermanium; tenuazonic acid; triaziquone; 2,2', 2"-trichlorotriethylamine; trichothecenes (especially T-2 toxin, verracurin A, roridin A and anguidine); urethan; vindesine (ELDISINEO, FILDESIN); dacarbazine; mannomustine; mitobronitol; mitolactol; pipobroman; gacytosine; arabinoside ("Ara-C"); thiotepa; taxoids, e.g., TAXOL paclitaxe), ABRAXANE Cremophor-free, albumin-engineered nanoparticle formulation of paclitaxel (American Pharmaceutical Partners, Schaumberg, Ill.), and TAXOTERE doxetaxel (Rhone-Poulenc Rorer, Antony, France); chloranbucil; gemcitabine (GEMZAR); 6-thioguanine; mercaptopurine; methotrexate; platinum analogs such as cisplatin and carboplatin; vinblastine (VELBAN); platinum; etoposide (VP-16); ifosfamide; mitoxantrone; vincristine (ONCOVIN); oxaliplatin; leucovovin; vinorelbine (NAVELBINE); novantrone; edatrexate; daunomycin; aminopterin; ibandronate; topoisomerase inhibitor RFS 2000; difluorometlhylornithine (DMFO); retinoids such as retinoic acid; capecitabine (XELODA); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN) combined with 5-FU and leucovovin.

Also included in this definition of chemotherapeutic agents are anti-hormonal agents that act to regulate, reduce, block, or inhibit the effects of hormones that can promote the growth of cancer, and are often in the form of systemic or whole-body treatment. They may be hormones themselves.

Another group of compounds that may be selected as neurological drugs for cancer treatment or prevention are anti-cancer immunoglobulins (including, but not limited to, trastuzumab, pertuzumab, bevacizumab, alemtuxumab, cetuximab, gemtuzumab ozogamicin, ibritumomab tiuxetan, panitumumab and rituximab). In some instances, antibodies in conjunction with a toxic label or conjugate may be used to target and kill desired cells (i.e., cancer cells), including, but not limited to, tositumomab with a $^{131}$I radiolabel, or trastuzumab emtansine.

Viral or microbial infections of the CNS include, but are not limited to, infections by viruses (i.e., influenza, HIV, poliovirus, rubella,), bacteria (i.e., *Neisseria* sp., *Streptococcus* sp., *Pseudomonas* sp., *Proteus* sp., *E. coli, S. aureus*, Pneumococcus sp., Meningococcus sp., *Haemophilus* sp., and *Mycobacterium tuberculosis*) and other microorganisms such as fungi (i.e., yeast, *Cryptococcus neoformans*), parasites (i.e., *Toxoplasma gondii*) or amoebas resulting in CNS pathophysiologies including, but not limited to, meningitis, encephalitis, myelitis, vasculitis and abscess, which can be acute or chronic.

For a viral or microbial disease, a neurological drug may be selected that includes, but is not limited to, an antiviral compound (including, but not limited to, an adamantane antiviral (i.e., rimantadine and amantadine), an antiviral interferon (i.e., peginterferon alfa-2b), a chemokine receptor antagonist (i.e., maraviroc), an integrase strand transfer inhibitor (i.e., raltegravir), a neuraminidase inhibitor (i.e., oseltamivir and zanamivir), a non-nucleoside reverse transcriptase inhibitor (i.e., efavirenz, etravirine, delavirdine and nevirapine), a nucleoside reverse transcriptase inhibitors (tenofovir, abacavir, lamivudine, zidovudine, stavudine, entecavir, emtricitabine, adefovir, zalcitabine, telbivudine and didanosine), a protease inhibitor (i.e., darunavir, atazanavir, fosamprenavir, tipranavir, ritonavir, nelfinavir, amprenavir, indinavir and saquinavir), a purine nucleoside (i.e., valacyclovir, famciclovir, acyclovir, ribavirin, ganciclovir, valganciclovir and cidofovir), and a miscellaneous antiviral (i.e., enfuvirtide, foscarnet, palivizumab and fomivirsen)), an antibiotic (including, but not limited to, an aminopenicillin (i.e., amoxicillin, ampicillin, oxacillin, nafcillin, cloxacillin, dicloxacillin, flucoxacillin, temocillin, azlocillin, carbenicillin, ticarcillin, mezlocillin, piperacillin and bacampicillin), a cephalosporin (i.e., cefazolin, cephalexin, cephalothin, cefamandole, ceftriaxone, cefotaxime, cefpodoxime, ceftazidime, cefadroxil, cephradine, loracarbef, cefotetan, cefuroxime, cefprozil, cefaclor, and cefoxitin), a carbapenemipenem (i.e., imipenem, meropenem, ertapenem, faropenem and doripenem), a monobactam (i.e., aztreonam, tigemonam, norcardicin A and tabtoxinine-beta-lactam, a beta-lactamase inhibitor (i.e., clavulanic acid, tazobactam and sulbactam) in conjunction with another beta-lactam antibiotic, an aminoglycoside (i.e., amikacin, gentamicin, kanamycin, neomycin, netilmicin, streptomycin, tobramycin, and paromomycin), an ansamycin (i.e., geldanamycin and herbimycin), a carbacephem (i.e., loracarbef), a glycopeptides (i.e., teicoplanin and vancomycin), a macrolide (i.e., azithromycin, clarithromycin, dirithromycin, erythromycin, roxithromycin, troleandomycin, telithromycin and spectinomycin), a monobactam (i.e., aztreonam), a quinolone (i.e., ciprofloxacin, enoxacin, gatifloxacin, levofloxacin, lomefloxacin, moxifloxacin, norfloxacin, ofloxacin, trovafloxacin, grepafloxacin, sparfloxacin and temafloxacin), a sulfonamide (i.e., mafenide, sulfonamidochrysoidine, sulfacetamide, sulfadiazine, sulfamethizole, sulfanilamide, sulfasalazine, sulfisoxazole, trimethoprim, trimethoprim and sulfamethoxazole), a tetracycline (i.e., tetracycline, demeclocycline, doxycycline, minocycline and oxytetracycline), an antineoplastic or cytotoxic antibiotic (i.e., doxorubicin, mitoxantrone, bleomycin, daunorubicin, dactinomycin, epirubicin, idarubicin, plicamycin, mitomycin, pentostatin and valrubicin) and a miscellaneous antibacterial compound (i.e., bacitracin, colistin and polymyxin B)), an antifungal (i.e., metronidazole, nitazoxanide, tinidazole, chloroquine, iodoquinol and paromomycin), and an antiparasitic (including, but not limited to, quinine, chloroquine, amodiaquine, pyrimethamine, sulphadoxine, proguanil, mefloquine, atovaquone, primaquine, artemesinin, halofantrine, doxycycline, clindamycin, mebendazole, pyrantel pamoate, thiabendazole, diethylcarbamazine, ivermectin, rifampin, amphotericin B, melarsoprol, eflornithine and albendazole).

Inflammation of the CNS includes, but is not limited to, inflammation that is caused by an injury to the CNS, which can be a physical injury (i.e., due to accident, surgery, brain trauma, spinal cord injury, concussion) and an injury due to or related to one or more other diseases or disorders of the CNS (i.e., abscess, cancer, viral or microbial infection). For CNS inflammation, a neurological drug may be selected that addresses the inflammation itself (i.e., a nonsteroidal anti-inflammatory agent such as ibuprofen or naproxen), or one which treats the underlying cause of the inflammation (i.e., an anti-viral or anti-cancer agent).

Ischemia of the CNS, as used herein, refers to a group of disorders relating to aberrant blood flow or vascular behavior in the brain or the causes therefor, and includes, but is not limited to: focal brain ischemia, global brain ischemia, stroke (i.e., subarachnoid hemorrhage and intracerebral hemorrhage), and aneurysm. For ischemia, a neurological drug may be selected that includes, but is not limited to, a thrombolytic (i.e., urokinase, alteplase, reteplase and tenecteplase), a platelet aggregation inhibitor (i.e., aspirin, cilostazol, clopidogrel, prasugrel and dipyridamole), a statin (i.e., lovastatin, pravastatin, fluvastatin, rosuvastatin, atorvastatin, simvastatin, cerivastatin and pitavastatin), and a compound to improve blood flow or vascular flexibility, including, e.g., blood pressure medications.

Neurodegenerative diseases are a group of diseases and disorders associated with neural cell loss of function or death in the CNS, and include, but are not limited to: adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia.

For a neurodegenerative disease, a neurological drug may be selected that is a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-Ira), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

Seizure diseases and disorders of the CNS involve inappropriate and/or abnormal electrical conduction in the CNS, and include, but are not limited to epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures).

For a seizure disorder, a neurological drug may be selected that is an anticonvulsant or antiepileptic including, but not limited to, barbiturate anticonvulsants (i.e., primidone, metharbital, mephobarbital, allobarbital, amobarbital, aprobarbital, alphenal, barbital, brallobarbital and phenobarbital), benzodiazepine anticonvulsants (i.e., diazepam, clonazepam, and lorazepam), carbamate anticonvulsants (i.e. felbamate), carbonic anhydrase inhibitor anticonvulsants (i.e., acetazolamide, topiramate and zonisamide), dibenzazepine anticonvulsants (i.e., rufinamide, carbamazepine, and oxcarbazepine), fatty acid derivative anticonvulsants (i.e., divalproex and valproic acid), gamma-aminobutyric acid analogs (i.e., pregabalin, gabapentin and vigabatrin), gamma-aminobutyric acid reuptake inhibitors (i.e., tiagabine), gamma-aminobutyric acid transaminase inhibitors (i.e., vigabatrin), hydantoin anticonvulsants (i.e. phenytoin, ethotoin, fosphenytoin and mephenytoin), miscellaneous anticonvulsants (i.e., lacosamide and magnesium sulfate), progestins (i.e., progesterone), oxazolidinedione anticonvulsants (i.e., paramethadione and trimethadione), pyrrolidine anticonvulsants (i.e., levetiracetam), succinimide anticonvulsants (i.e., ethosuximide and methsuximide), triazine anticonvulsants (i.e., lamotrigine), and urea anticonvulsants (i.e., phenacemide and pheneturide).

Behavioral disorders are disorders of the CNS characterized by aberrant behavior on the part of the afflicted subject and include, but are not limited to: sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like).

For a behavioral disorder, a neurological drug may be selected from a behavior-modifying compound including, but not limited to, an atypical antipsychotic (i.e., risperidone, olanzapine, apripiprazole, quetiapine, paliperidone, asenapine, clozapine, iloperidone and ziprasidone), a phenothiazine antipsychotic (i.e., prochlorperazine, chlorpromazine, fluphenazine, perphenazine, trifluoperazine, thioridazine and mesoridazine), a thioxanthene (i.e., thiothixene), a miscellaneous antipsychotic (i.e., pimozide, lithium, molindone, haloperidol and loxapine), a selective serotonin reuptake inhibitor (i.e., citalopram, escitalopram, paroxetine, fluoxetine and sertraline), a serotonin-norepinephrine reuptake inhibitor (i.e., duloxetine, venlafaxine, desvenlafaxine, a tricyclic antidepressant (i.e., doxepin, clomipramine, amoxapine, nortriptyline, amitriptyline, trimipramine, imipramine, protriptyline and desipramine), a tetracyclic antidepressant (i.e., mirtazapine and maprotiline), a phenylpiperazine antidepressant (i.e., trazodone and nefazodone), a monoamine oxidase inhibitor (i.e., isocarboxazid, phenelzine, selegiline and tranylcypromine), a benzodiazepine (i.e., alprazolam, estazolam, flurazeptam, clonazepam, lorazepam and diazepam), a norepinephrine-dopamine reuptake inhibitor (i.e., bupropion), a CNS stimulant (i.e., phentermine, diethylpropion, methamphetamine, dextroamphetamine, amphetamine, methylphenidate, dexmethylphenidate, lisdexamfetamine, modafinil, pemoline, phendimetrazine, benzphetamine, phendimetrazine, armodafinil, diethylpropion, caffeine, atomoxetine, doxapram, and mazindol), an anxiolytic/sedative/hypnotic (including, but not limited to, a barbiturate (i.e., secobarbital, phenobarbital and mephobarbital), a benzodiazepine (as described above), and a miscellaneous anxiolytic/sedative/hypnotic (i.e. diphenhydramine, sodium oxybate, zaleplon, hydroxyzine, chloral hydrate, aolpidem, buspirone, doxepin, eszopiclone, ramelteon, meprobamate and ethclorvynol)), a secretin (see, e.g., Ratliff-Schaub et al. *Autism* 9: 256-265 (2005)), an opioid peptide (see, e.g., Cowen et al., *J. Neurochem.* 89:273-285 (2004)), and a neuropeptide (see, e.g., Hethwa et al. *Am. J. Physiol.* 289: E301-305 (2005)).

Lysosomal storage disorders are metabolic disorders which are in some cases associated with the CNS or have CNS-specific symptoms; such disorders include, but are not limited to: Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

For a lysosomal storage disease, a neurological drug may be selected that is itself or otherwise mimics the activity of the enzyme that is impaired in the disease. Exemplary recombinant enzymes for the treatment of lysosomal storage disorders include, but are not limited to those set forth in e.g., U.S. Patent Application publication no. 2005/0142141 (i.e., alpha-L-iduronidase, iduronate-2-sulphatase, N-sulfatase, alpha-N-acetylglucosaminidase, N-acetyl-galactosamine-6-sulfatase, beta-galactosidase, arylsulphatase B, beta-glucuronidase, acid alpha-glucosidase, glucocerebrosidase, alpha-galactosidase A, hexosaminidase A, acid sphingomyelinase, beta-galactocerebrosidase, beta-galactosidase, arylsulfatase A, acid ceramidase, aspartoacylase, palmitoyl-protein thioesterase 1 and tripeptidyl amino peptidase 1).

The above-described therapeutic composition agent can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Nucleic acid molecules can be administered using techniques known in the art, including via vector, plasmid, liposome, DNA injection, electroporation, gene gun, intravenously injection or hepatic artery infusion. Vectors (including viral vectors) for use in gene therapy embodiments are known in the art.

According to a specific embodiment, the method of the invention allows for water flux from the brain to the blood in a highly controlled manner. The therapeutic composition may be used in combination with a hypertonic solution. Advantageously, the therapeutic composition and hypertonic solution may be administered concurrently at the same time.

Macroscopic Imaging

In another aspect, this invention provides a novel noninvasive transcranial macroscopic imaging approach that allows one to track cortical CSF flow in real time in the intact brain of a living subject. The method comprises introducing an effective amount of an imaging agent to the central nervous system of a subject, and imaging the brain of the subject.

The imaging agent can be delivered intracisternally or intrathecally. In a preferred embodiment, the imaging agent comprises a fluorophore and the step of imaging comprises fluorescence macroscopy. In example, the fluorophore re-emit light in the infrared region (e.g., the near infrared region, the mid infrared region, or the far-infrared region) upon excitation.

As disclosed herein, this new imaging approach exploiting the brain-wide system of perivascular spaces to quickly and effectively enhance delivery of therapeutics. To this end, this invention also provides a novel transcranial optical imaging approach enabling non-invasive and dynamic measurements of CSF transport. With that, one can obtain brain-wide imaging of CSF tracers, in contrast to the narrow field visualized by 2-photon microscopy, while obtaining spatial and temporal resolution that is not attainable with MRI. The high frame rate acquisition is compatible with the use of front-tracking software to quantify CSF transport in the rodent brain by measuring progress of the tracer front at pixel level resolution (56). The macroscope has a large gantry to image small animals in immobilized or behaving configurations (e.g., running wheels or cognitive tests). The placement of non-invasive chronic cyanoacrylate cranial windows enables repeat imaging (57). Accordingly, transcranial optical imaging can be applied to intracerebroventricular or intraparenchymal tracer studies in order to evaluate clearance.

Kit and Articles of Manufacture

In another aspect of the invention, this invention provides a kit or an article of manufacture containing materials useful for the methods described above. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective (1) for improving delivery of a composition to a central nervous system interstitium, brain interstitium and/or a spinal cord interstitium of a subject or (2) for treating, preventing and/or diagnosing one or more of the conditions mentioned above. The container may have a sterile access port (for example, the container may be an intravenous solution bag or a vial having a stopper pierceable by a hypodermic injection needle). At least one active agent in the composition can be a macromolecule therapeutic, e.g., an antibody. The label or package insert indicates that the composition is used for treating the condition of choice.

Moreover, the article of manufacture may comprise (a) a first container with a composition contained therein, wherein the composition comprises an agent that enhances glymphatic system influx and (b) a second container with a composition contained therein, wherein the composition comprises a therapeutic agent or imaging agent. The article of manufacture in this embodiment of the invention may further comprise a package insert indicating that the compositions can be used to treat a particular condition. Alternatively, or additionally, the article of manufacture may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, the kit or article of manufacture further comprises instructional materials containing directions (i.e., protocols) for the practice of the methods described herein (e.g., instructions for using the kit for administering a composition). While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD-ROM), and the like. Such media may include addresses to internet sites that provide such instructional materials.

Definitions

As used herein, the "osmolality" of a solution is the number of osmoles of solute per kilogram of solvent. Osmolality is a measure of the number of particles present in solution and is independent of the size or weight of the particles. It can be measured only by use of a property of the solution that is dependent only on the particle concentration. These properties are vapour pressure depression, freezing point depression, boiling point elevation, and osmotic pressure, and are collectively referred to as colligative properties. The "osmolarity" of a solution is the number of osmoles of solute per liter of solution.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids. The term "protein" as used herein refers to either a polypeptide or a dimer (i.e., two) or multimer (i.e., three or more) of single chain polypeptides. The single chain polypeptides of a protein may be joined by a covalent bond, e.g., a disulfide bond, or non-covalent interactions.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. A "nucleic acid fragment" is a fraction of a given nucleic acid molecule. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. An "antibody fragment" refers to a molecule other than an intact antibody that comprises a portion of an intact antibody that binds the antigen to which the intact antibody binds. Examples of antibody fragments are well known in the art (see, e.g., Nelson, MAbs (2010) 2(1): 77-83) and include but are not limited to Fab, Fab', Fab'-SH, F(ab')$_2$, and Fv; diabodies; linear antibodies; single-chain antibody molecules including but not limited to single-chain variable fragments (scFv), fusions of light and/or heavy-chain antigen-binding domains with or without a linker (and optionally in tandem); and monospecific or multispecific antigen-binding molecules formed from antibody fragments (including, but not limited to multispecific antibodies constructed from multiple variable domains which lack Fc regions).

"Anti-Aβ antibody" refers to an antibody that specifically binds to human AD. A nonlimiting example of an anti-Aβ antibody is crenezumab. Other non-limiting examples of anti-Aβ antibodies are solanezumab, bapineuzumab, gantenerumab, aducanumab, ponezumab and any anti-Abeta antibodies disclosed in the following publications: WO2000162801, WO2002046237, WO2002003911, WO2003016466, WO2003016467, WO2003077858, WO2004029629, WO2004032868, WO2004032868, WO2004108895, WO2005028511, WO2006039470, WO2006036291, WO2006066089, WO2006066171, WO2006066049, WO2006095041, and WO2009027105.

A "neurological disorder" refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS, including brain metastases resulting from cancer elsewhere in the body).

A "neurological disorder drug" is a drug or therapeutic agent that treats one or more neurological disorder(s). Neurological disorder drugs of the invention include, but are not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Non-limiting examples of neurological disorder drugs and the disorders they may be used to treat are provided herein.

The term "cytotoxic agent" refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

As used herein, an "inhibitory nucleic acid" is a double-stranded RNA, RNA interference, miRNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

A "therapeutic RNA molecule" or "functional RNA molecule" as used herein can be an antisense nucleic acid, a ribozyme (e.g., as described in U.S. Pat. No. 5,877,022), an RNA that effects spliceosome-mediated trans-splicing (see, Puttaraju et al. (1999) Nature Biotech. 17:246; U.S. Pat. Nos. 6,013,487; 6,083,702), an interfering RNA (RNAi) including siRNA, shRNA or miRNA, which mediate gene silencing (see, Sharp et al., (2000) Science 287:2431), and any other non-translated RNA, such as a "guide" RNA and CRISPR RNA (Gorman et al. (1998) Proc. Nat. Acad. Sci. USA 95:4929; U.S. Pat. No. 5,869,248) and the like as are known in the art.

"Anti-sense" refers to a nucleic acid sequence, regardless of length, that is complementary to the coding strand or mRNA of a nucleic acid sequence. Antisense RNA can be introduced to an individual cell, tissue or organanoid. An anti-sense nucleic acid can contain a modified backbone, for example, phosphorothioate, phosphorodithioate, or other modified backbones known in the art, or may contain non-natural internucleoside linkages.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

As used herein, the term "siRNA" intends a double-stranded RNA molecule that interferes with the expression of a specific gene or genes post-transcription. In some embodiments, the siRNA functions to interfere with or inhibit gene expression using the RNA interference pathway. Similar interfering or inhibiting effects may be achieved with one or more of short hairpin RNA (shRNA), microRNA (mRNA) and/or nucleic acids (such as siRNA, shRNA, or miRNA) comprising one or more modified nucleic acid residue—e.g. peptide nucleic acids (PNA), locked nucleic acids (LNA), unlocked nucleic acids (UNA), or triazole-linked DNA. Optimally, a siRNA is 18, 19, 20, 21, 22, 23 or 24 nucleotides in length and has a 2-base overhang at its 3' end. These dsRNAs can be introduced to an individual cell or culture system. Such siRNAs are used to downregulate mRNA levels or promoter activity.

An "imaging agent" is a compound that has one or more properties that permit its presence and/or location to be detected directly or indirectly. Examples of such imaging agents include proteins and small molecule compounds incorporating a labeled moiety that permits detection. An imaging agent can be any chemical or substance that is used to provide the signal or contrast in imaging. Examples include an organic molecule, metal ion, salt or chelate, particle, labeled peptide, protein, polymer or liposome.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, the polypeptides described herein are administered intravenously.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

An "effective amount" of an agent, e.g., a pharmaceutical formulation, refers to an amount effective, at dosages and for periods of time necessary, to achieve the desired therapeutic or prophylactic result.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, the term "pharmaceutical composition" refers to the active agent in combination with a pharmaceutically acceptable carrier commonly used in the pharmaceutical industry.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion.

Alternatively, in some contexts, the term "vector" may be used to refer to the vector genome/vDNA alone.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term "about" means within an acceptable error range for the particular value.

EXAMPLES

Example 1 Material and Methods

This example describes material and methods used in Examples 2-5 bellow.

Animals. For all experiments, male C57BL/6 mice, 8-12 weeks of age (Charles River) were used. Male global aquaporin-4 knockout (Aqp4$^{-/-}$) mice on a C57BL/6 background, between 8-12 weeks old, were used where indicated (21). Male 6-month-old APP/PS1$^{+/-}$ mice (Jackson Laboratory) were used for the Aβ antibody experiments.

Intracisternal injections. Mice in the KX groups were weighed and anesthetized with a mixture of ketamine (100 mg/kg, i.p.) and xylazine (10 mg/kg, i.p.). Afterwards, animals were fixed in a stereotaxic frame, and the cisterna magna was surgically exposed with the help of a stereomicroscope. The cisternal space was cannulated using a 30G needle attached via polyethylene tubing to a Hamilton syringe. The needle was secured with cyanoacrylate glue and tracers were infused with a syringe pump (Harvard Apparatus) depending on the experimental paradigm (see below). Mice randomized to the awake group were anesthetized with 2% isoflurane, their skull cemented to a customized head plate, placed in a restraint tube, and then underwent the same surgical procedure as described above. Tracers were allowed to circulate for 30 min after the injection start time and the needle left in place for the duration of the experiment to prevent the CSF compartment from depressurizing. Core temperature (37° C.) and anesthetic depth were maintained throughout the experiment. At the end of 30 min, animals were decapitated, and the brain processed for either fluorescent or radioisotope tracer analysis.

CSF Tracers. AlexaFluor647-conjugated bovine serum albumin (BSA-647, 66 kDa, Invitrogen) was constituted in artificial CSF (0.5% m/v) and used as a fluorescent CSF tracer. Radio-labeled $^1$C-inulin (6 kDa, Perkin Elmer) and $^3$H-dextran (40 kDa, American Radiolabeled Chemicals) were dissolved in artificial CSF at a concentration of 0.1 and 10 μCi/μL, respectively. For APP/PS1 experiments, an AlexaFluor488-conjugated anti-β-amyloid antibody (clone 6E10, 1 mg/mL; BioLegend, Cat. No. 803013) was infused and allowed to circulate for 120 min. Fluorescent tracers and antibodies were infused in a total volume of 10 μl at a rate of 2 μl/min or 1 μl/min into the cisterna magna. Radioisotope tracers were infused in a total volume of 5 μl at 1 μl/min. A direct comparison of 2 μl/min and 1 μl/min infusion rate showed no difference in BSA-647 influx on in vivo imaging (P=0.971, two-way repeated measures ANOVA) or ex vivo coronal sections (P=0.939, unpaired t test).

Transcranial In vivo Macroscopic Imaging. For in vivo imaging, the skin covering the dorsal calvarium was incised and reflected laterally prior to cannulating the cisterna magna. The entry of CSF tracers into the brain was imaged by fluorescence macroscopy (MVX10, Olympus) using a PRIOR Lumen 1600-LED light source and Flash 4.0 digital camera (Hamamatsu). The mouse fixed on the stereotaxic frame was placed on the microscope stage and images at 20× magnification were acquired in the far-red emission channel (647 nm). Images (2048×2048 pixel; 5.7120 μm/pixel) were collected at 1 min intervals for 0-30 min following injection commencement using the MetaMorph Basic imaging software (Molecular Devices). Exposure time was held constant throughout the duration of the imaging sequence and across experimental groups.

Front tracking. To quantify the area and speed of fluorescent CSF tracer influx in the brain, inventors employed an algorithm recently developed in the context of advection-reaction-diffusion (56). Given a time series of a two-dimensional concentration field, this algorithm tracked the location of the "front" which separates low-concentration and high-concentration regions. The algorithm outputs spatially- and temporally-resolved velocity measurements quantifying the front propagation. Influx speed was calculated by averaging over the entire group data to obtain mean front speed measurements for each group. The propagation front was identified using a threshold of 175 (on an 8-bit scale of 0 to 255); however, it was noted that the results were fairly robust to different threshold choices. This same threshold was used for all-time series of images, which was justified since care was taken to maintain similar imaging conditions across all experiments. A fixed threshold preserved the physical meaning of the front and allowed for quantitative comparison between populations from different experiments. More details and a copy of the code, written for MATLAB (MathWorks), are available online (56).

In vivo two-photon imaging. A 3 mm cranial window was placed over the right parietal bone of anesthetized mice. The window was covered with agarose (0.8% at 37° C.) and sealed with a glass coverslip. Imaging was done using a resonant scanner B scope (Thorlabs) with a Chameleon Ultra II laser (Coherent) and a water-immersion 20× objective (1.0 NA, Olympus). Intravascular fluorescein isothiocyanate-dextran (FITC-dextran, 2,000 kDa) was given prior to a CM tracer infusion of bovine serum albumin conjugated to Texas Red (BSA-TxRd, 66 kDa). Z-stacks were taken over the MCA every minute from the start of the infusion for 30 minutes. To measure CSF influx, three circular regions of interest (ROI) were outlined on the perivascular space and measurements for each ROI were taken at every timepoint (ThorImageLS). Fluorescence intensity for all three ROIs were averaged and normalized to the peak fluorescence ($\Delta F/F_{max}$) and expressed as a percent. Time to tracer appearance was calculated as the first timepoint where fluorescence was above background signal. Orthogonal reconstructions were done using Imaris (Bitplane).

Solutions. Control mice received isosmotic saline (0.34M NaCl in ddH$_2$O; 20 μL/g, i.p.). Hyperosmolality was induced either with mannitol (1M in 0.34M NaCl; 30 μL/g, i.p.) or hypertonic saline (1M NaCl in ddH$_2$O; 20 μL/g, i.p.). Thirty minutes after intraperitoneal injection, a plasma sample was taken, and the mouse decapitated. Plasma osmolality was measured in triplicate using a micro-osmometer (Advanced Instruments).

Brain Water Content Measurement. Brains were dissected and immediately weighed ($w_{wet}$; g). The tissue was dried at 65° C. until they reached a constant weight (~48 hours). Brains were re-weighed ($w_{dry}$) and the tissue water content (m/g dry weight) calculated $$\frac{w_{wet} - w_{dry}}{(w_{dry})}.$$

Intracranial and Arterial Blood Pressure Measurements. A separate group of animals were anesthetized with a mixture of ketamine/xylazine. Afterwards, a 30G needle connected to rigid polyethylene tubing filled with aCSF was inserted into the cisterna magna as described above and an arterial catheter was placed in the femoral artery. The lines were connected to a pressure transducer and monitor (World Precision Instruments). Recordings were allowed to stabilize, and then recorded continuously for 35 min (5 min baseline and 30 min after i.p. injection). The signals were digitized and recorded with a DigiData 1440A digitizer and AxoScope software (Axon Instruments). The intracranial and mean arterial pressure recordings were processed and analyzed using MATLAB (MathWorks).

Laser Doppler Flowmetry. Relative changes in cerebral blood flow (rCBF) were measured using laser Doppler flowmetry (PF5010 Laser Doppler Perfusion Module with microtips, PR 418-1, Perimed). The tip of the fiber optic probe was fixed directly onto the exposed skull with cyanoacrylate glue. Signals were collected using a 1440A digitizer and AxoScope software (Axon Instruments). For each mouse, rCBF was recorded both 5 minutes before and 30 minutes after the administration of i.p. solutions. The rCBF recordings were processed and analyzed using MATLAB (MathWorks).

Assessment of BBB Permeability. For quantification of BBB disruption, a 1% solution of FITC-conjugated dextran (70 kDa; Sigma-Aldrich) in normal saline (4 mL/kg of body weight) was injected via the femoral vein. The dextran was allowed to circulate for 30 min following plasma tonicity manipulations, at which point a plasma sample was taken and the mice were perfusion-fixed as described below. Positive controls received a 2M mannitol infusion via a catheter in the right external carotid artery (0.64 mL/min for 30 seconds) 5 minutes after the dextran. The brains were harvested, sectioned, and FITC extravasation was imaged and quantified (see below). Plasma concentration of the FITC dextran was calculated by diluting the plasma samples 1:4 with PBS and analyzing them in triplicate on a fluorescence microplate reader (SpectraMax M2, Molecular Devices) at 458 nm excitation, 538 nm emission, with a cutoff above 530 nm at room temperature (24° C.). Dextran concentration was estimated by comparing the relative fluorescence of the samples against a standard curve (0.0-1.0 mg/mL, 0.1 mg/mL steps; FITC-dextran 70 kDa in PBS) fitted with a linear regression. Blood samples with hemolysis were excluded from analysis due to interference with spectrophotometric absorbance readings.

Imaging Depth Analysis. The depth of fluorescence detection using macroscopic imaging is highly dependent on the power of the illumination source, excitation/emission wavelength of the fluorophore, and the exposure time. However, inventors attempted to estimate the depth of detection for transcranial optical imaging. For this, anesthetized mice were imaged using the macroscope while receiving an intracisternal infusion of BSA-647 as before. Images were acquired every 60 seconds for a duration of either 5, 10, 15, 20, 25, or 30 minutes. Mice were sacrificed immediately following the corresponding stop time; brains were harvested and drop fixed in 4% PFA overnight and then sectioned (see below). Tracer fluorescence was quantified in coronal sections to determine the depth of fluorescence detection (see Image Analysis). In a separate set of experiments, penetration depth of imaging was calculated for a 635 nm wavelength. To determine the optimal tracer concentration for imaging, BSA-647 was serially diluted (10 to $1\times10^{-4}$ mg/ml by increments of 10) and 10 µl were aliquoted into a black 96-well plate. Each well was imaged on the macroscope using the same magnification and exposure time as the in vivo experiments (100 ms). Afterwards, a capillary was loaded with 0.1 mg/ml BSA-647, sealed on both sides, and embedded in a petri dish with 4% agarose, level with the surface. Acute coronal slices of increasing thickness (200-4000 µm) were obtained from control mice and sections were placed over the dye-filled capillary for imaging. The slices were maintained in aCSF during imaging so as to preserve the optical properties of the tissue.

Amyloid-β Plaque Labeling. APP/PSi mice were injected intraperitoneally with methoxy-X04 (MeX04, Tocris, 10 mg/kg, i.p.) dissolved in DMSO (10%), propylene glycol (45%), and PBS (45%) 24 hours prior to cisterna magna injections, as previously described (59).

Tissue Collection and Processing. For fluorescent CSF tracer influx analysis, mice were decapitated after 30 min of the injection start and the brains drop-fixed in 4% paraformaldehyde (PFA; Sigma-Aldrich) overnight at 4° C. Brains were harvested and fixed within 30 seconds of the completion of image acquisition. For assessment of BBB permeability, mice were transcardially perfused with ice-cold 0.1M PBS (pH 7.4, Sigma-Aldrich) followed by 4% PFA. Brain tissue was carefully dissected away from the skull and dura then post-fixed overnight in 4% PFA at 4° C. For immunohistochemistry, mice were perfusion-fixed as before but FITC-conjugated lectin from *Triticum vulgaris* (25 µg/mL; Sigma-Aldrich) was added into the ice-cold PBS solution prior to the PFA perfusion step. For the APP/PS1 experiments, mice were lectin-perfused as above but with an AlexaFluor647-conjugated wheat germ agglutinin (WGA) lectin (15 µg/mL; Invitrogen).

Immunohistochemistry. To confirm if CSF tracers entered the brain via para-arterial spaces, coronal slices were stained for AQP4 using a free-float method. Slices were blocked for 1 h at room temperature (7% normal donkey serum, NDS, in 0.5% Triton in PBS) and then incubated with primary rabbit anti-AQP4 (1:500; 1% NDS in 0.1% Triton/PBS, Millipore, Cat. No. AB3594) antibody overnight at 4° C. The sections were then incubated with a secondary Cy3-conjugated donkey anti-rabbit (1:250; Jackson ImmunoResearch Cat. No. 711-165-152) antibody for 2 hours at room temperature and washed. Brain sections were mounted with ProLong Gold Antifade with DAPI (Invitrogen) and allowed to dry for 24 h before imaging.

Ex vivo Fluorescence Imaging. Prior to sectioning, dorsal whole brain images were acquired for CSF tracer (BSA-647) on a stereomicroscope (MVX10, Olympus) at 16× magnification. Afterwards, coronal slices (100 µm thickness) were obtained using a calibrated vibratome (VT1200S, Leica). Beginning at the anterior aspect of the corpus callosum, one section was collected every 5 sections until a total of 6 sections had been acquired for each animal. Brain sections were mounted with ProLong Gold Antifade with DAPI (Invitrogen) and with Fluoromount-G (SouthernBiotech) for MeX04 experiments. The entry of CSF tracer into the brain was evaluated by epifluorescence macroscopy (MVX10, Olympus). Single channel images were acquired with the MetaMorph Basic software (Molecular Devices) at low magnification (20×). Exposures were determined based on control brains and held constant for all groups. To better visualize tracer movement into the brain, inventors imaged coronal slices with a CSF tracer (BSA-647), intravital lectin (FITC), and stained for AQP4 (Cy3) on a laser scanning confocal microscope (IX81, Olympus) using FluoView (FV500, Olympus) software. Multi-channel images from both left and right dorsal cortex were acquired (40 µm z-stacks with 2 µm step size at 40× magnification). In APP/PS1 mice, coronal sections were imaged at 4× magnification using a montage epifluorescence microscope (BX51 Olympus and CellSens Software) and high magnification 20× and 100× images on confocal (Leica SP8 and LASX software).

Image Analysis. All images were analyzed using ImageJ software (National Institutes of Health, imagej.nih.gov/ij/) (60). To measure glymphatic influx in vivo, a customized macro was developed. A region of interest (ROI) was defined based upon the exposed skull perimeter and overlaid on a 31-image (8-bit; 2048×2048 pixels) stack collected over the imaging session. The macro quantified mean pixel intensity for each time point (0-30 min). Images were pseudo-colored using an ImageJ lookup table (Jet) to better display pixel intensity (0-255). Tracer and antibody penetration were also quantified ex vivo in coronal sections, as described previously[1]. Each slice was analyzed for mean pixel intensity and the average was computed for all 6 sections taken from one brain. For Aβ plaque quantification, 4× montage coronal images were analyzed using Fiji (61). Images were automatically thresholded (Yen method) on the MeX04 channel and ROIs were generated for each plaque. Plaque burden was calculated from the mean number of plaques per $cm^2$ from 3 coronal sections in each mouse. The thresholded MeX04 image was converted into a mask and used to calculate percent MeX04-positive area. A mask was generated for the Aβ antibody fluorescence following the same process and the percent area that was both MeX04- and A$ antibody-positive over the total MeX04-positive area was considered target engagement. The same coronal sections were used to perform a nearest neighbor analysis of the co-labeled plaques and the closest perivascular space using Fiji and Amira (FEI). The three-dimensional reconstruction was done using Amira (FEI) from 100× confocal z-stacks (0.5 µm step sizes, Leica SP8). To estimate the depth of fluorescence detection, mean pixel intensity for seven regions of interest, each 1-mm deep, from the dorsal convexity to the base of the brain (total 7 mm) were drawn for six coronal sections from an individual mouse using Fiji. Background fluorescence was calculated from all the coronal slices of the 5 min time point and the threshold for signal was placed 2 standard deviations above background. An average for all the 1 mm ROIs from each coronal section was calculated for individual mice. Tracer was considered present when MPI from all mice in the group were higher than the threshold. BBB permeability to FITC-dextran was quantified as percent area in six coronal sections for each mouse using a thresholding approach. The threshold was established using Fiji (Otsu) on all coronal sections from the positive control group and computing an average for all slices. The average threshold level was then applied to all the sections from the experimental groups.

Radioisotope Influx. To evaluate solute influx into the brain, radiolabeled tracers 3H-dextran (50 μCi) and $^{14}$C-inulin (0.5 μCi) were injected into the cisterna magna as described above. After 30 min, animals were rapidly decapitated, the skull and dura removed, and the brain harvested. Brain radioactivity was normalized to the total radioactivity detected in a 5 μL aliquot put directly into a scintillation vial immediately before intracisternal injection. All brain tissue was weighed and solubilized in 0.5 mL tissue solubilizer (Solvable, PerkinElmer) overnight. Upon solubilization, 5 mL of scintillation cocktail was added (Ultima Gold, PerkinElmer). The injectate controls were treated in the same way as the tissue samples. All samples were analyzed by liquid scintillation spectrometry using a scintillation counter (LS 6500 Multipurpose Scintillation Counter, Beckman Coulter). The radioactivity (disintegrations per minute: dpm) remaining in the brain after injection (percent of injected dose: % ID) was determined as $$\frac{R_b}{R_i} \times 100,$$

where $R_b$ is the radioactivity remaining in the brain at the end of the experiment and $R_1$ is the radioactivity in the injectate controls for each experiment. Influx percentage was deduced as % ID. Dextran and inulin are inert, polar molecules that are not actively transported within the CNS, and due to their difference in molecular weight, they are ideal tracers for evaluating the presence of bulk flow.

Statistical Analysis. All statistical testing was performed on GraphPad Prism 7 (GraphPad Software). Tests were chosen based on the data set being analyzed and are reported in the figure legends. All statistical testing was two-tailed and exact P values were calculated at a 0.05 level of significance. All values are expressed as the mean±SEM, unless otherwise stated.

Study approval. All experiments adhered to the laws of the United States, regulations of the Department of Agriculture, and performed according to guidelines from the National Institutes of Health. Experiments were approved by the University Committee on Animal Resources of the University of Rochester (Protocol No. 2011-023) and an effort was made to minimize the number of animals used.

Example 2 In Vivo Transcranial Fluorescence Macroscopy Allowed Non-Invasive Brain-Wide Imaging of Glymphatic Flow and Confirms 2-Photon and Ex Vivo Microscopic Findings of Reduced CSF Influx in Awake and Aqp4$^{-/-}$ Mice Prior studies of CSF-interstitial fluid (ISF) exchange within the glymphatic system have utilized ex vivo conventional fluorescence microscopy and in vivo 2-photon microscopy to image CSF- or ISF-based tracer fluxes (21, 22, 28, 29, 35, 36). While superior for evaluation of brain-wide glymphatic function, including its detailed cellular and molecular organization, ex vivo imaging of brain sections lacks dynamic temporal information, requiring that indirect inferences be made about temporal patterns and rates of glymphatic flow. Conversely, in vivo 2-photon imaging permits real-time determination of rates of CSF tracer appearance in cerebral tissues in individual mice, albeit with a relatively narrow field of view and shallow imaging depth (21, 28, 29).

Consequently, inventors developed a new technique for non-invasive in vivo time-lapse imaging of transcranial glymphatic flows using fluorescence macroscopy. (FIG. 5). The technique consists of imaging fluorescent tracers delivered into the cisterna magna of live rodents through an intact skull using an LED illumination source for fluorophore excitation and a macro zoom microscope with high-efficiency CMOS camera for fluorescence detection. The tunable LED can achieve fast-switching between wavelengths and quad filter cubes allow for high-speed, multi-channel image acquisition. The macroscope has a wide field of view enabling mesoscopic imaging of the entire cortical surface and a penetration depth of up to 1-2 mm (FIG. 6).

In validating this technique, inventors first replicated prior in vivo and ex vivo findings of reduced glymphatic CSF influx in awake mice and mice lacking AQP4 (Aqp4$^{-/-}$) (21, 28). Anesthetized mice in all groups had reflection of the scalp overlying the dorsal calvarium, and cannula placement within the cisterna magna. Groups of wild type and Aqp4$^{-/-}$ mice were subsequently maintained under ketamine/xylazine (KX) anesthesia (KX and KX-Aqp4$^{-/-}$), while a separate group of wild type mice had a metallic plate secured to the skull for head immobilization, and were then placed in a plastic restraint tube prior to waking up (Awake).

Figures 1A, 1B, 1C, 1D, 1E, 1F, 1G:
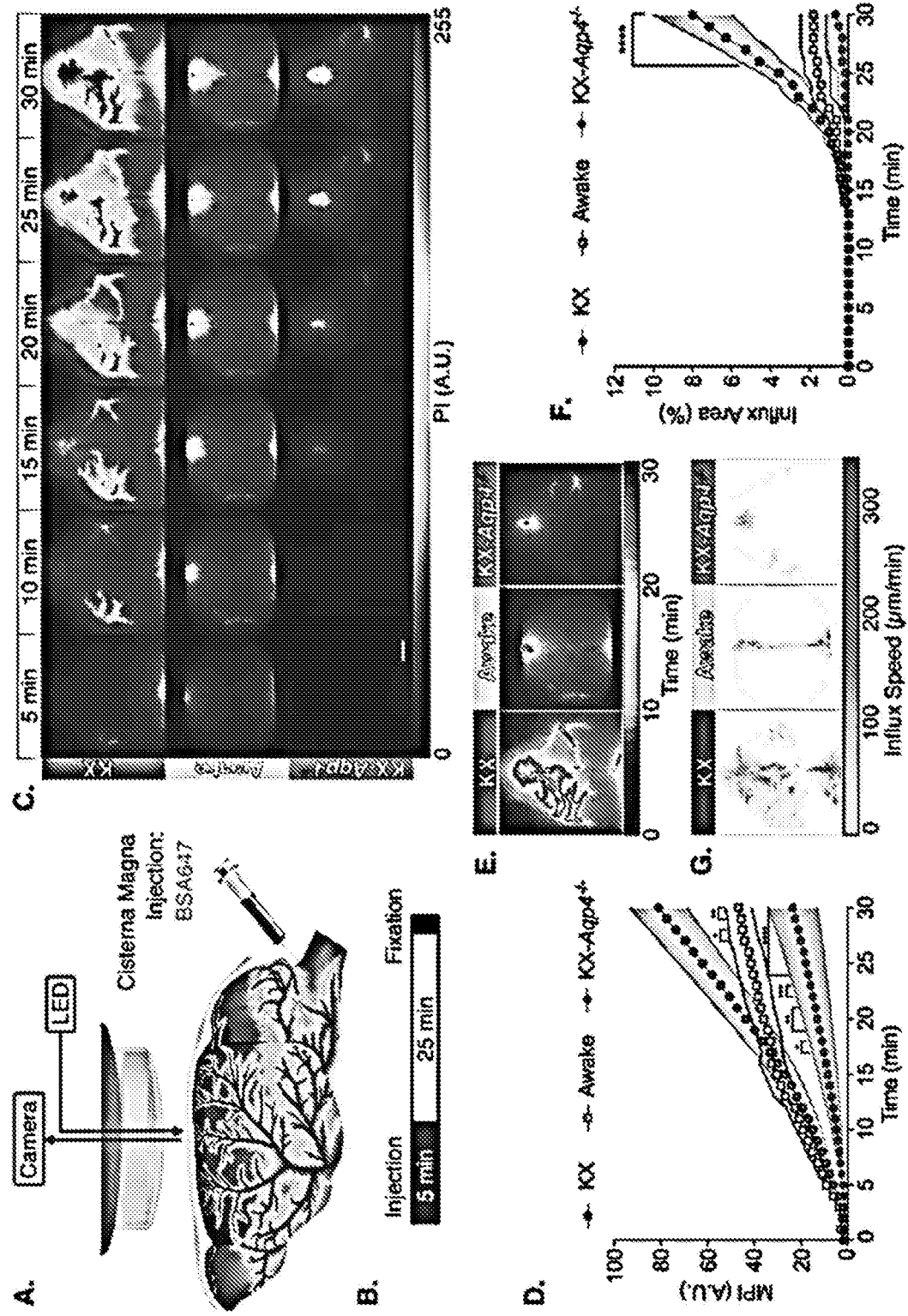
FIGS. 1A, 1B, 1C, 1D, 1E, 1F, 1G, 1H and 1I are a set of diagrams and photographs showing in vivo transcranial brain-wide imaging of CSF influx. (A). Mice were imaged through an intact skull using a macroscope. (B) A fluorescent protein tracer (BSA-647 nm) was delivered into the cisterna magna (2 μL/min, 5 min) and tracer influx was imaged for 30 min from the start of the injection. All mice received i.p. isotonic saline at the onset of the intracisternal injection. (C) Representative time-lapse images of CSF influx over the first 30 minutes following tracer injection in anesthetized (KX) and awake wild type mice, as well as anesthetized Aqp4$^{-/-}$ mice (KX-Aqp4$^{-/-}$). Images (8-bit pixel depth) are color-coded to depict pixel intensity (PI) in arbitrary units (A.U.). Scale bar=2 mm. Fluorescence was detected as early as 5 min after infusion at the base of the brain approximately 5-6 mm below the dorsal cortical surface. (D) Quantification of mean pixel intensity (MPI) for the 30-minute in vivo imaging series depicted in (c) (mean±SEM; n=5-7 mice/group; repeated measures two-way ANOVA, Sidak's multiple comparisons test; *P<0.05, P<0.01, *P<0.001, **P<0.0001 vs. KX). (E) Representative front-tracking analysis of CSF tracer influx over the imaging session. Fronts are time-coded in minutes. (F) Quantification of the influx area over time from analysis (e) (mean±SEM; n=5-7 mice/group; repeated measures two-way ANOVA, Sidak's multiple comparisons test; **P<0.0001 KX vs. Awake and KX- Aqp4$^{-/-}$). (G) Average influx speed maps (μm/min) generated from group data in (c) and (e). (H) Representative conventional fluorescence images of brains ex vivo upon removal from the cranium (bottom left; scale bar=2 mm) and after coronal sectioning to evaluate tracer penetrance deep into the cortical surface (top; scale bar=1 mm) in the KX and awake wild type, and KX-anesthetized Aqp4$^{-/-}$ groups. High magnification images of perivascular tracer were acquired using laser scanning confocal microscopy (bottom right; scale bar=50 μm). (I) Quantification of ex vivo coronal section fluorescence MPI for the KX and awake wild type, and KX-anesthetized Aqp4$^{-/-}$ groups (mean±SEM; n=3-8 mice/group; one-way ANOVA, Tukey's multiple comparisons test; *P<0.05, **P<0.01).
Figures 1H, 1I:
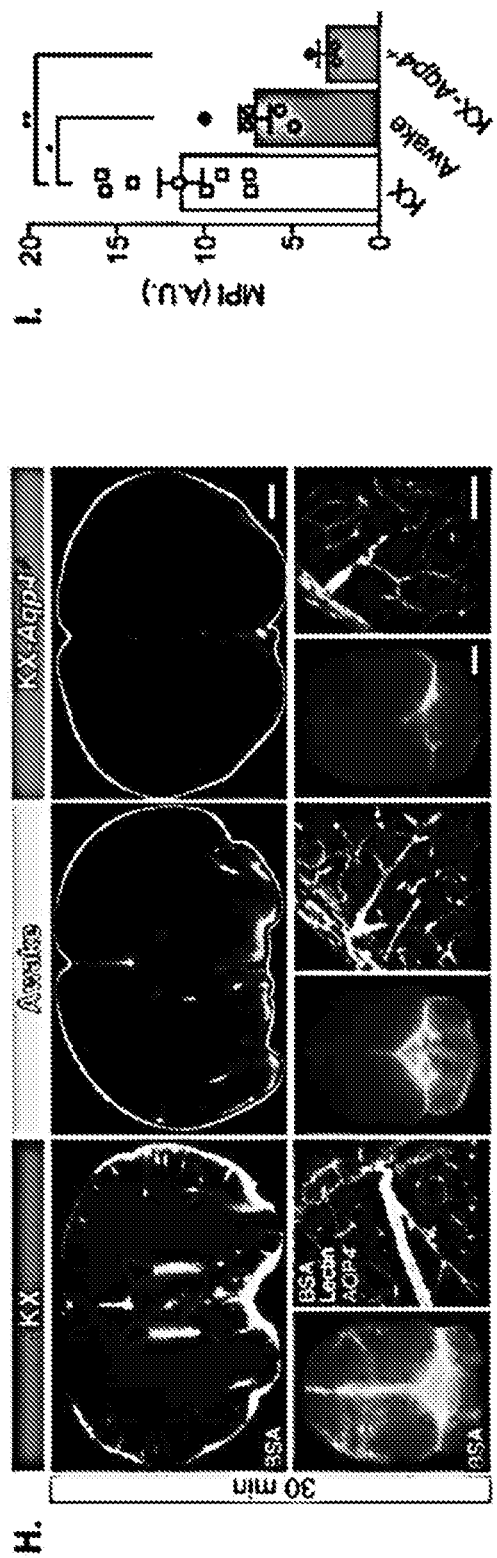

Subsequently, mice were moved to the stage of a fluorescence macroscope for dynamic image acquisition, AlexaFluor647-conjugated bovine serum albumin (BSA-647, 66 kDa) was injected into the cisterna magna (FIGS. 1A and B). Intracisternal infusion caused a mild, transient increase in ICP that normalized before the appearance of tracer (30). Fluorescence was detectable as soon as the tracers arrived in the basal cistern approximately 5-6 mm below the cortical surface (FIG. 7). The influx of BSA-647 into the brain was imaged over 30 minutes before brain harvesting and fixation in 4% paraformaldehyde (PFA) and washed in buffer (FIG. 1B).

In both anesthetized and awake mice, this transcranial macroscopic approach revealed a pattern of glymphatic CSF influx identical to that previously characterized using in vivo 2-photon (FIG. 8) and ex vivo imaging techniques. The fluorescent protein tracer first appeared within the large rostral and caudal subarachnoid spaces, such as the olfactofrontal cistern and pineal recess, and was carried within minutes over the dorsal cerebral convexity within pial periarterial spaces (FIG. 8); this topography followed the territories of the anterior and posterior cortical segments of the middle cerebral artery (MCA; FIGS. 8 and 9).

It was noted that the infusion pump was stopped at five minutes, or when faint fluorescent signal was first noted at the base of the MCA, indicating that all subsequent tracer appearance could be attributed to physiologic bulk flow. Towards the end of the 30-minute imaging experiment, tracer started to accumulate within the PVS of cortical bridging veins adjacent to the dural sinuses. Confirming previously reported findings, there was significantly less glymphatic influx in both the awake and KX-Aqp4$^{-/-}$ groups compared to the KX mice (FIGS. 1C and D). Interestingly, at the 30-minute time point, glymphatic influx was significantly lower in anesthetized Aqp4$^{-/-}$ mice than in the awake group (FIG. 1D), suggesting that effect on glymphatic function due to deletion of water channels exceeded effects of state of consciousness.

As described above, prior studies of CSF-based delivery of intrathecal solutes to brain could not simultaneously quantify the surface area covered by the tracer and influx kinetics. Even MRI, despite a unique ability to characterize spatial distribution and temporal dynamics, lacks the spatial resolution required to evaluate CSF flows at the level of the PVS (22). Using front-tracking analysis in combination with a macroscopic imaging paradigm to overcome this limitation, we could demonstrate that CSF flow within pial peri-arterial spaces was higher in KX anesthetized mice and occupied approximately 10% of the dorsal cortical surface compared with under 2% in the awake and KX-Aqp4$^{-/-}$ groups (FIG. 1E-G). Further, in the awake and knockout groups, perivascular spaces were essentially devoid of tracer, with most of the fluorescent area confined to the olfactofrontal cistern (FIG. 1E).

To exclude the possibility that the imaged glymphatic fluxes were occurring exclusively within the subarachnoid space, the harvested brains underwent conventional fluorescence imaging ex vivo. This analysis showed that the distribution of fluorescent signal throughout the dorsal cortex matched that seen at the terminal 30-minute time point of the sequence in vivo (FIG. 10), thus supporting that the CSF flows observed with the macroscope were occurring at the tissue level and not within the subarachnoid space.

Following coronal sectioning, brain slices were imaged to determine the degree of tracer penetrance into deeper cerebral structures. Again, in parallel to observations during the in vivo imaging series, significantly less tracer was present in brain tissue of the awake and KX-Aqp4$^{-/-}$ mice than in the KX group (FIG. 1H, top panels; I1). Finally, high resolution confocal images showed that perivascular space tracer distribution was higher in the KX cohort than in the awake and KX-Aqp4$^{-/-}$ mice (FIG. 1H, bottom right panels), confirming the in vivo observation of absent perivascular influx within these groups, and confirming that tracer influx does not occur via diffusion along the pial surface (27).

Collectively, these findings validate the use of fluorescence macroscopy for brain-wide, transcranial imaging of in vivo glymphatic CSF influx, and recapitulate prior work demonstrating the dependence of these flows on perivascular AQP4 expression and the enlargement of interstitial space volume that accompanies sleep (21, 28). Additionally, these new data suggest that increased resistance to fluid flow between the perivascular and interstitial spaces due to AQP4 deletion has a much more profound suppressive effect on glymphatic flow than does wakefulness-related contraction of the interstitial space. The recent critique of the key role of AQP4 in glymphatic function (37) has been challenged by a recent study from four independent labs demonstrating an essential role of AQP4 in solute dispersion in the mouse brain (38).

Example 3 Plasma Hyperosmolality Significantly Increased CSF Influx in Anesthetized Mice In this example, assays were carried out to study whether plasma hyperosmolality could enhance the delivery of CSF-based tracers to a greater volume of brain and whether such enhancement occurs via the network of perivascular spaces comprising the glymphatic pathway.

Plasma hypertonicity is often induced clinically for the treatment of elevated ICP using either hypertonic saline (HTS) or mannitol infusions (49). For evaluating effects on glymphatic function, both hypertonicity methods were used to exclude specificity for HTS or mannitol. Briefly, KX-anesthetized wild type mice prepared as above received an intraperitoneal (i.p.) injection of either isotonic saline (KX), hypertonic saline (+HTS), or hypertonic mannitol (+Mannitol) (FIGS. 11A and 11B), consistently resulting in significantly elevated plasma osmolality lasting 30 minutes (FIGS. 11C-E). Notably, at the plasma tonicities achieved in the HTS and mannitol-injected mice, there was no significant increase in BBB permeability (FIGS. 12A-C). In both treatment groups, immediately following intraperitoneal injection of isotonic or hypertonic solutions, BSA-647 was injected to the cisterna magna, and the tracer's area of distribution and kinetics were imaged for 30 minutes using the transcranial microscopic approach described above (FIG. 2A). In agreement with prior studies (27, 50, 51), the main route of CSF tracer entry into brain was via the perivascular spaces surrounding the MCA (FIG. 2B).

These data show that in response to a volume regulatory challenge, the perivascular spaces indeed act as fast conduits to deliver subarachnoid CSF into the volume-depleted brain. However, even more striking was the finding that plasma hypertonicity, due either to HTS or mannitol challenge, led to a nearly five-fold increase in the influx area, with CSF tracer covering approximately 60% of the dorsal cortical surface, while reducing the time to delivery by roughly half (FIGS. 2C and D). We saw significantly increased influx speeds over the entire cortical surface in the HTS and mannitol groups relative to the isotonic controls (FIGS. 2E and F). This effect was independent of AQP4 expression as plasma hypertonicity was able to override the inhibition of CSF influx seen in Aqp4$^{-/-}$ mice, to levels comparable with wildtypes (FIG. 13).

To rule out the possibility that this enhanced tracer influx was limited to the subarachnoid space, the brain and leptomeninges were removed from the calvarium, and cerebral tissues washed prior to conventional ex vivo fluorescence microscopy. Here, the pattern of tracer distribution mirrored that seen at the 30-minute time point of the in vivo imaging experiment, with most of the tracer occupying the subpial or pial perivascular spaces (FIG. 2G, bottom left panels vs 2B, panels under 30 min). Further, imaging of coronal brain sections showed significantly greater tracer signal at locations deep within the brain parenchyma of the HTS and mannitol groups, evidently having been carried into brain via the perivascular spaces of cortical penetrating arteries (FIG. 2G, top and bottom right panels; 2H). Correlation analysis revealed a strong positive relationship between fluorescence signal captured using the newly described in vivo transcranial macroscopic approach, as well as ex vivo whole brain fluorescence, and the traditionally acquired signal from ex vivo coronal sections (FIGS. 14A and B), again suggesting that in vivo tracer dynamics are reflective of tissue level CSF and solute fluxes.

Finally, as the relationship between the amount of fluorescent tracer and relative fluorescence units is linear only at sub-saturated signal levels, we used two radioisotope tracers, $^3$H-dextran (40 kDa) and $^{14}$C-inulin (6 kDa), to quantify hypertonicity-induced enhancement of glymphatic CSF influx to cerebral tissues. To confirm that entry of tracer within the brain parenchyma was not an artefact of the infusion paradigm, but truly represented physiologic bulk flow, we injected the radioisotope tracers to the cisternal CSF at a rate and volume half that of the fluorescent tracers (1 vs 2 μL/min, respectively over 5 min). We found a roughly 125% increase in the fractional tracer uptake to brain, with approximately 40% of the total injected tracer being delivered to the brain parenchyma in both conditions of plasma hyperosmolality (FIGS. 2I and J). Notably, using plasma osmolality as the predictor, linear regression analysis of tissue radioisotope uptake versus in vivo transcranial or ex vivo coronal section fluorescence area showed significant positive relationships, with similar regression slopes (FIGS. 14C and D). These two independent lines of evidence support the concept that bulk flow mediates tracer influx irrespective of the more than 10-fold difference in molecular weight between fluorescent and radioisotope tracers, and further suggests that non-invasively acquired in vivo fluorescence data and terminal radioisotope studies both offer similarly quantitative assessment of glymphatic dynamics.

Example 4 Plasma Hyperosmolality Overrides Arousal State-Dependent Inhibition of Glymphatic Function As prior studies have demonstrated profound suppression of glymphatic function in conditions of arousal (28), assays were carried out to examiner whether plasma hypertonicity could overcome wakefulness-related inhibition of CSF influx. Using a similar approach as above, after intraperitoneal injection of either isotonic saline, HTS, or hypertonic mannitol, awake mice received an intracisternal injection of BSA-647 and underwent transcranial macroscopic imaging for a 30-min period prior to brain removal and fixation (FIG. 3A).

Surprisingly, it was found that front-tracking analysis of the in vivo transcranial imaging sequence showed that plasma hyperosmolality evoked a circa 20-fold increase in tracer influx area at 30 min (FIG. 3B-D). Further, tracer influx rates were roughly 1.5-fold faster across the entire dorsal cortex in the awake hyperosmolar challenge groups (FIGS. 3E and F). Finally, inspection of coronal sections showed significantly increased tracer influx to deep cerebral structures in both the HTS and mannitol-injected groups, matching observations in the KX-anesthetized cohort. Again, this enhanced tracer influx tended to occur via the perivascular spaces of penetrating arteries (FIGS. 3G and H).

Hyperosmolar agents such as HTS and mannitol have previously been shown to influence mean arterial blood pressure (MAP), cerebral blood flow, and ICP (52, 53). Consequently, assays were carried out to determine if tonicity-induced changes in one of these parameters might be responsible for the observed enhancement of glymphatic CSF influx. Here, it was found that both hyperosmolar challenges reduced MAP, but the effect of HTS was transient, resolving within 15-20 min of intraperitoneal injection (FIG. 15A). Similarly, while there was a slight reduction in relative cerebral blood flow (rCBF) following mannitol administration, rCBF was preserved throughout the duration of the 30-min recording in the HTS group (FIG. 15B). On the contrary, ICP significantly and consistently declined in both hyperosmolar groups relative to the isotonic controls (FIG. 15C). This net negative ICP resulted from the outflow of ISF across the BBB (FIG. 15D), and likely provided the necessary driving force to increase CSF influx to cerebral tissues. Importantly, this transfer of brain water to the vascular column occurred across an intact BBB (FIGS. 12A-C).

Example 5 Plasma Hyperosmolality Rescues Glymphatic Transport in 6-Month-Old APP/PS1 Mice and Enhances Delivery and Target Engagement of an Anti-Aβ Antibody Having demonstrated in conditions of both anesthesia and wakefulness that plasma hyperosmolality increases CSF influx to brain, inventors next sought to determine if this paradigm could be used as a tool to improve brain-wide distribution of experimental therapeutics via the glymphatic pathway. Consequently, it was asked whether plasma hypertonicity could rescue impairment of glymphatic CSF influx in a murine transgenic model of AD (APP/PS1$^{+/-}$), and further whether an enhancement in glymphatic function could improve brain-wide delivery of an anti-Aβ antibody and its interaction with both perivascular and parenchymal Aβ plaques.

Using an approach similar to that described above, KX anesthetized 6-month old APP/PS1$^{+/-}$ mice received an intraperitoneal injection of either isotonic saline (Control) or hypertonic saline (+HTS) immediately prior to intracisternal delivery of an AlexaFluor488-conjugated anti-Aβ antibody (clone 6E10), which circulated for 120 min prior to brain removal and fixation (FIGS. 4A and B). One day prior to intracisternal antibody injection, intravital labelling of Aβ plaques was obtained with intraperitoneal MeX04 (FIG. 4B). HTS was used to enhance CSF influx due to its lack of effect on rCBF and only transient influence on MAP (FIGS. 15A and B).

It was found that the HTS reversed the glymphatic impairment previously documented in the APP/PS1$^{+/-}$ mice (35) and provoked significantly increased anti-Aβ antibody delivery throughout the cerebrum relative to the isotonic controls. Further, the antibody appeared to gain access to the brain parenchyma via the perivascular spaces (FIGS. 4C and D). While the anti-Aβ antibody was restricted to penetrating arterial perivascular spaces in the control group, there was significant antibody engagement with MeX04$^+$ plaques in the HTS-treated mice, suggesting that plasma hypertonicity brings about re-distribution of perivascular solutes to deeper interstitial sites (FIG. 4C, bottom right panels; 4E and F). This is supported by the nearest neighbor analysis showing greater co-labeled plaque distance from the nearest perivascular space in the +HTS group relative to isotonic controls (FIG. 4G).

The greatest abundance of co-labeled plaques occurred in the area immediately surrounding penetrating arteries, with declining frequency at greater distance from the perivascular space. However, nearly all co-labeled plaques occurred within 100 μm of the nearest periarterial space in the control group, whereas this mean separation increased to over 300 μm in the HTS group (FIG. 4H). Three-dimensional reconstructions of confocal z-stacks demonstrated increased antibody binding to plaque surfaces in the +HTS group, although, interestingly, there were no significant differences in plaque burden between groups (FIG. 4I-K). This is likely due to the acute setting of the experiment, being terminated after 120 min of antibody engagement. It is expected that more extended periods of enhanced plaque engagement in the setting of plasma hypertonicity ultimately reduces plaque burden and rescues cognitive performance in AD mice. Present observations also extend the prior finding that genetic deletion of AQP4 in APP/PS1 transgenic mice accelerated cognitive decline and amyloid burden (54).

REFERENCES

1. Sevigny J et al. The antibody aducanumab reduces Abeta plaques in Alzheimer's disease. *Nature*. 2016; 537(7618): 50-6.
2. Schenk D B et al. First-in-human assessment of PRX002, an anti-alpha-synuclein monoclonal antibody, in healthy volunteers. *Mov Disord*. 2017; 32(2):211-218.
3. Gros-Louis F, Soucy G, Lariviere R, Julien J P. Intracerebroventricular infusion of monoclonal antibody or its derived Fab fragment against misfolded forms of SOD1 mutant delays mortality in a mouse model of ALS. *J Neurochem*. 2010; 113(5):1188-99.

4. Gallardo G, Holtzman D M. Antibody Therapeutics Targeting Abeta and Tau. *Cold Spring Harb Perspect Med.* 2017; 7(10)
5. Sampson J H, Maus M V, June C H. Immunotherapy for Brain Tumors. *J Clin Oncol.* 2017; 35(21):2450-2456.
6. Selkoe D J, Hardy J. The amyloid hypothesis of Alzheimer's disease at 25 years. *EMBO Mol Med.* 2016; 8(6): 595-608.
7. Klyubin I et al. Amyloid beta protein immunotherapy neutralizes Abeta oligomers that disrupt synaptic plasticity in vivo. *Nat Med.* 2005; 11(5):556-61.
8. Salloway S et al. Two phase 3 trials of bapineuzumab in mild-to-moderate Alzheimer's disease. *N Engl J Med.* 2014; 370(4):322-33.
9. Doody R S et al. Phase 3 trials of solanezumab for mild-to-moderate Alzheimer's disease. *N Engl J Med.* 2014; 370(4):311-21.
10. Honig L S et al. Trial of Solanezumab for Mild Dementia Due to Alzheimer's Disease. *N Engl J Med.* 2018; 378 (4):321-330.
11. Vandenberghe R et al. Bapineuzumab for mild to moderate Alzheimer's disease in two global, randomized, phase 3 trials. *Alzheimers Res Ther.* 2016; 8(1):18.
12. Brody D L, Holtzman D M. Active and passive immunotherapy for neurodegenerative disorders. *Annu Rev Neurosci.* 2008; 31:175-93.
13. Calias P, Banks W A, Begley D, Scarpa M, Dickson P. Intrathecal delivery of protein therapeutics to the brain: a critical reassessment. *Pharmacol Ther.* 2014; 144(2):114-22.
14. Cohen-Pfeffer J L et al. Intracerebroventricular Delivery as a Safe, Long-Term Route of Drug Administration. *Pediatr Neurol.* 2017; 67:23-35.
15. Prins N D, Scheltens P. Treating Alzheimer's disease with monoclonal antibodies: current status and outlook for the future. *Alzheimers Res Ther.* 2013; 5(6):56.
16. Banks W A, Terrell B, Farr S A, Robinson S M, Nonaka N, Morley J E. Passage of amyloid beta protein antibody across the blood-brain barrier in a mouse model of Alzheimer's disease. *Peptides.* 2002; 23 (12):2223-6.
17. Banks W A, Farr S A, Morley J E, Wolf K M, Geylis V, Steinitz M. Anti-amyloid beta protein antibody passage across the blood-brain barrier in the SAMP8 mouse model of Alzheimer's disease: an age-related selective uptake with reversal of learning impairment. *Exp Neurol.* 2007; 206(2):248-56.
18. Salloway S, Sperling R, Brashear H R. Phase 3 trials of solanezumab and bapineuzumab for Alzheimer's disease. *N Engl J Med.* 2014; 370(15):1460.
19. Thakker D R et al. Intracerebroventricular amyloid-beta antibodies reduce cerebral amyloid angiopathy and associated micro-hemorrhages in aged Tg2576 mice. *Proc Natl Acad Sci USA.* 2009; 106(11):4501-6.
20. Sperling R A et al. Amyloid-related imaging abnormalities in amyloid-modifying therapeutic trials: recommendations from the Alzheimer's Association Research Roundtable Workgroup. *Alzheimers Dement.* 2011; 7(4): 367-85.
21. Iliff J J et al. A paravascular pathway facilitates CSF flow through the brain parenchyma and the clearance of interstitial solutes, including amyloid beta. *Sci Transl Med.* 2012; 4(147):147ra111.
22. Iliff J J et al. Brain-wide pathway for waste clearance captured by contrast-enhanced MRI. *J Clin Invest.* 2013; 123 (3): 1299-309.
23. Jessen N A, Munk A S, Lundgaard I, Nedergaard M. The Glymphatic System: A Beginner's Guide. *Neurochem Res.* 2015; 40(12):2583-99.
24. Rennels M L, Gregory T F, Blaumanis O R, Fujimoto K, Grady P A. Evidence for a 'paravascular' fluid circulation in the mammalian central nervous system, provided by the rapid distribution of tracer protein throughout the brain from the subarachnoid space. *Brain Res.* 1985; 326(1):47-63 .
25. Rennels M L, Blaumanis O R, Grady P A. Rapid solute transport throughout the brain via paravascular fluid pathways. *Adv Neurol.* 1990; 52:431-9.
26. Wolak D J, Pizzo M E, Thorne R G. Probing the extracellular diffusion of antibodies in brain using in vivo integrative optical imaging and ex vivo fluorescence imaging. *J Control Release.* 2015; 197:78-86.
27. Pizzo M E et al. Intrathecal antibody distribution in the rat brain: surface diffusion, perivascular transport, and osmotic enhancement of delivery. *J Physiol.* 2018; 596 (3):445-475.
28. Xie L et al. Sleep drives metabolite clearance from the adult brain. *Science.* 2013; 342(6156):373-7.
29. Kress B T et al. Impairment of paravascular clearance pathways in the aging brain. *Ann Neurol.* 2014; 76(6): 845-61.
30. Iliff J J et al. Cerebral arterial pulsation drives paravascular CSF-interstitial fluid exchange in the murine brain. *J Neurosci.* 2013; 33(46):18190-9.
31. Lee H et al. The Effect of Body Posture on Brain Glymphatic Transport. *J Neurosci.* 2015; 35(31):11034-44.
32. Pullen R G, DePasquale M, Cserr H F. Bulk flow of cerebrospinal fluid into brain in response to acute hyperosmolality. *Am J Physiol.* 1987; 253(3 Pt 2):F538-45.
33. Cserr H F, DePasquale M, Patlak C S. Volume regulatory influx of electrolytes from plasma to brain during acute hyperosmolality. *Am J Physiol.* 1987; 253(3 Pt 2):F530-7.
34. Cserr H F, DePasquale M, Nicholson C, Patlak C S, Pettigrew K D, Rice M E. Extracellular volume decreases while cell volume is maintained by ion uptake in rat brain during acute hypernatremia. *J Physiol.* 1991; 442:277-95.
35. Peng W et al. Suppression of glymphatic fluid transport in a mouse model of Alzheimer's disease. *Neurobiol Dis.* 2016; 93:215-25.
36. Yang L et al. Evaluating glymphatic pathway function utilizing clinically relevant intrathecal infusion of CSF tracer. *J Transl Med.* 2013; 11:107.
37. Smith A J, Yao X, Dix J A, Jin B J, Verkman A S. Test of the 'glymphatic' hypothesis demonstrates diffusive and aquaporin-4-independent solute transport in rodent brain parenchyma. *Elife.* 2017; 6.
38. Mestre H et al. Aquaporin-4 dependent glymphatic solute transport in rodent brain. *bioRxiv.* 2017.
39. Lundgaard I et al. Glymphatic clearance controls state-dependent changes in brain lactate concentration. *J Cereb Blood Flow Metab.* 2017; 37(6):2112-2124.
40. Murlidharan G, Crowther A, Reardon R A, Song J, Asokan A. Glymphatic fluid transport controls paravascular clearance of AAV vectors from the brain. *JCI Insight.* 2016; 1(14):e88034.
41. Jiang Q et al. Impairment of the glymphatic system after diabetes. *J Cereb Blood Flow Metab.* 2017; 37(4):1326-1337.
42. Rangroo Thrane V et al. Paravascular microcirculation facilitates rapid lipid transport and astrocyte signaling in the brain. *Sci Rep.* 2013; 3:2582.

43. Achariyar T M et al. Glymphatic distribution of CSF-derived apoE into brain is isoform specific and suppressed during sleep deprivation. *Mol Neurodegener.* 2016; 11(1): 74.
44. Lundgaard I et al. Direct neuronal glucose uptake heralds activity-dependent increases in cerebral metabolism. *Nat Commun.* 2015; 6:6807.
45. Venkat P et al. White matter damage and glymphatic dysfunction in a model of vascular dementia in rats with no prior vascular pathologies. *Neurobiol Aging.* 2017; 50:96-106.
46. Benveniste H et al. Anesthesia with Dexmedetomidine and Low-dose Isoflurane Increases Solute Transport via the Glymphatic Pathway in Rat Brain When Compared with High-dose Isoflurane. *Anesthesiology.* 2017; 127(6): 976-988.
47. Gaberel T et al. Impaired glymphatic perfusion after strokes revealed by contrast-enhanced MRI: a new target for fibrinolysis? *Stroke.* 2014; 45(10):3092-6.
48. Ringstad G, Vatnehol S A S, Eide P K. Glymphatic MRI in idiopathic normal pressure hydrocephalus. *Brain.* 2017; 140(10):2691-2705 .
49. Brain Trauma F, American Association of Neurological S, Congress of Neurological S, Joint Section on N, Critical Care A C, Bratton S L, et al. Guidelines for the management of severe traumatic brain injury. I I. Hyperosmolar therapy. *J Neurotrauma.* 2007; 24 Suppl 1:S14-20.
50. Ma Q, Ineichen B V, Detmar M, Proulx S T. Outflow of cerebrospinal fluid is predominantly through lymphatic vessels and is reduced in aged mice. *Nat Commun.* 2017; 8 (1):1434.
51. Bedussi B et al. Paravascular channels, cisterns, and the subarachnoid space in the rat brain: A single compartment with preferential pathways. *J Cereb Blood Flow Metab.* 2017; 37(4):1374-1385.
52. Muizelaar J P, Lutz H A 3rd, Becker D P. Effect of mannitol on ICP and CBF and correlation with pressure autoregulation in severely head-injured patients. *J Neurosurg.* 1984; 61 (4):700-6.
53. Domaingue C M, Nye D H. Hypotensive effect of mannitol administered rapidly. *Anaesth Intensive Care.* 1985; 13 (2):134-6.
54. Xu Z et al. Deletion of aquaporin-4 in APP/PS1 mice exacerbates brain Abeta accumulation and memory deficits. *Mol Neurodegener.* 2015; 10:58.
55. Golde T E. Open questions for Alzheimer's disease immunotherapy. *Alzheimers Res Ther.* 2014; 6(1):3.
56. Nevins T D, Kelley D H. Front tracking for quantifying advection-reaction-diffusion. *Chaos.* 2017; 27(4):043105.
57. Silasi G, Xiao D, Vanni M P, Chen A C, Murphy T H. Intact skull chronic windows for mesoscopic wide-field imaging in awake mice. *J Neurosci Methods.* 2016; 267: 141-9.
58. Demattos R B et al. A plaque-specific antibody clears existing beta-amyloid plaques in Alzheimer's disease mice. *Neuron.* 2012; 76(5):908-20.
59. Klunk W E et al. Imaging Abeta plaques in living transgenic mice with multiphoton microscopy and methoxy-X04, a systemically administered Congo red derivative. *J Neuropathol Exp Neurol.* 2002; 61(9):797-805.
60. Schneider C A, Rasband W S, Eliceiri K W. NIH Image to ImageJ: 25 years of image analysis. *Nat Methods.* 2012; 9(7):671-5.
61. Schindelin J et al. Fiji: an open-source platform for biological-image analysis. *Nat Methods.* 2012; 9 (7): 676-82.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method for improving delivery of a composition to a central nervous system interstitium, brain interstitium and/or a spinal cord interstitium of a subject comprising:
   (1) enhancing glymphatic system influx by administering a hypertonic solution into plasma of the subject via intravenous, intraarterial, or intraperitoneal delivery, wherein the hypertonic solution comprises NaCl or Mannitol and is hypertonic with respect to the blood of the subject; followed by
   (2) injecting the composition intracisternally or intrathecally to the central nervous system interstitium, brain interstitium and/or the spinal cord interstitium.
2. The method of claim 1, wherein the step of enhancing glymphatic system influx further comprises pumping fluid through the central nervous system interstitium.
3. The method of claim 1, wherein the hypertonic solution is administered via intravenous or intraperitoneal delivery.
4. The method of claim 1, wherein the composition is injected intrathecally.
5. The method of claim 1, wherein the composition is an imaging composition.
6. The method of claim 1, wherein the composition is a therapeutic composition.
7. The method of claim 1, wherein the composition comprises a small molecule, a virus, a large molecule, a peptide, an antibody, a nucleic acid, or a biologically active fragment thereof.
8. The method of claim 7, wherein the therapeutic composition comprises an antibody.
9. The method of claim 8, wherein the antibody is conjugated to a ligand that facilitates transport across the blood brain barrier (BBB).
10. The method of claim 9, wherein the ligand specifically binds to a blood-brain barrier (BBB) receptor.
11. A method for treating a neurological disorder in a subject, comprising
    (1) enhancing glymphatic system influx by administering a hypertonic solution into plasma of the subject via intravenous, intraarterial, or intraperitoneal delivery, wherein the hypertonic solution comprises NaCl or Mannitol and is hypertonic with respect to the blood of the subject; followed by
    (2) injecting a therapeutic composition intracisternally or intrathecally to the central nervous system interstitium, brain interstitium and/or the spinal cord interstitium.
12. The method of claim 11, wherein the step of enhancing glymphatic system influx further comprises pumping fluid through the central nervous system interstitium.
13. The method of claim 11, wherein the hypertonic solution is administered via intravenous or intraperitoneal delivery.

14. The method of claim 11, wherein the composition is injected intrathecally.

15. The method of claim 11, wherein the therapeutic composition comprises a small molecule, a virus, a large molecule, a peptide, an antibody, a nucleic acid, or a biologically active fragment thereof.

16. The method of claim 15 wherein the therapeutic composition comprises an antibody.

17. The method of claim 16, wherein the antibody is conjugated to a ligand that facilitates transport across the blood brain barrier.

18. The method of claim 17, wherein the ligand specifically binds to a BBB receptor.

19. The method of claim 16, wherein the antibody is an anti-Aβ antibody.

20. The method of claim 1, wherein the subject is a mammal.

21. The method of claim 20, wherein the mammal is a human or a non-human primate.

22. The method of claim 11, wherein the neurological disorder is selected from the group consisting of a neuropathy, an amyloidosis, cancer, an ocular disease or disorder, a viral or microbial infection, inflammation, ischemia, neurodegenerative disease, seizure, behavioral disorder, and lysosomal storage disease.

* * * * *